US010472397B2

(12) United States Patent
Federici et al.

(10) Patent No.: US 10,472,397 B2
(45) Date of Patent: Nov. 12, 2019

(54) USE OF CYT1AA AS BROAD SPECTRUM TARGETING DOMAIN FOR INSECTICIDAL PROTEINS WITH BASIC RESEARCH AND BIOTECHNOLOGY APPLICATIONS

(71) Applicants: Brian A. Federici, Riverside, CA (US); Dennis Bideshi, Corona, CA (US); Hyun-Woo Park, Riverside, CA (US); Robert Hice, Riverside, CA (US); Tianyun Su, Riverside, CA (US)

(72) Inventors: Brian A. Federici, Riverside, CA (US); Dennis Bideshi, Corona, CA (US); Hyun-Woo Park, Riverside, CA (US); Robert Hice, Riverside, CA (US); Tianyun Su, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/646,062

(22) Filed: Jul. 10, 2017

(65) Prior Publication Data
US 2018/0086796 A1     Mar. 29, 2018

Related U.S. Application Data

(60) Provisional application No. 62/360,096, filed on Jul. 8, 2016.

(51) Int. Cl.
*C07K 14/325*     (2006.01)
*C07K 14/32*     (2006.01)
*A01N 63/02*     (2006.01)

(52) U.S. Cl.
CPC ............ *C07K 14/325* (2013.01); *A01N 63/02* (2013.01); *C07K 14/32* (2013.01)

(58) Field of Classification Search
CPC ...... A01N 63/02; C07K 14/195; C07K 14/32; C07K 14/325; C07K 2319/00; C07K 2319/55; Y02A 50/356
See application file for complete search history.

(56) References Cited

FOREIGN PATENT DOCUMENTS

WO    WO-2010077672 A2 *   7/2010   ............. A01N 63/02

OTHER PUBLICATIONS

WHO Factsheet on the World Malaria report, Dec. 2014, on the World Wide Web at who.int/malaria/media/world_malaria_report_2014/en/.
Huang YJ, Higgs S, Horne KM, Vanlandingham DL (2014) Flavivirus-Mosquito Interactions. Viruses 6:4703-4730.
Mathai D, Vasanthan AG (2009) State of the Globe: Yellow Fever is Still Around and Active J Glob Infect Dis 1:4-6.
Enayati A, Hemingway J (2010) Malaria management: past, present, and future. Annu Rev Entomol 55:569-591.
Federici BA, Park H-W, Bideshi DK (2010) Overview of the basic biology of Bacillus thuringiensis with emphasis on genetic engineering of bacterial larvicides for mosquito control. Open Toxinol J 3:83-100.
Berry C (2012) The bacterium, *Lysinibacillus sphaericus*, as an insect pathogen. J Invertebr Pathol 109:1-10.
Palma L, Munoz D, Berry C, Murillo J, Caballero P (2014) Bacillus thuringiensis toxins: an overview of their biocidal activity. Toxins 6:3296-325.
Ben-Dov E (2014) *Bacillus thuringiensis* subsp. israelensis and its dipteran-specific toxins. Toxins 6:1222-1243.
Du J, Knowles BH, Li J, Ellar DJ (1999) Biochemical characterization of Bacillus thuringiensis cytolytic toxins in association with phospholipid bilayer. Biochem J 338:185-193.
Promdonkoy B, Ellar DJ (2000) Membrane pore architecture of a cytolytic toxin from Bacillus thuringiensis. Biochem J 350:275-282.
Wirth MC (2010) Mosquito resistance to bacterial larvicidal toxins. Open Toxinol J 3:101-115.
Cantón PE, López-Diaz JA; Gill SA, Bravo A, Soberón S (2014) Membrane binding and oligomer membrane insertion are necessary but insufficient for Bacillus thuringiensis Cyt1Aa toxicity. Peptides 53:286-291.
Butko P (2003) Cytolytic toxin Cyt1A and its mechanism of membrane damage: data and hypothesis. Appl Environ Microbiol 69:2415-2422.
Nicolas L, Nielsen-Leroux C, Charles J-F, Delecluse A (1993) Respective roles of the 42- and 51-kDa components of the Bacillus sphaericus toxin overexpressed in Bacillus thuringiensis, FEMS Microbiol Lett 106:275-280.
Charles J-F, Silva-Filha MH, Nielsen-LeRoux C, Humphreys, MJ, Berry, C (1997) Binding of the 51- and 42-kDa individual components from the Bacillus sphaericus crystal toxin to mosquito larval midgut membranes from *Culex* and *Anopheles* sp. (Diptera: Culicidae). FEMS Microbiol Letts 31:153-159.
Darboux I, Nielsen-LeRoux C, Charles J-F, Pauron D (2001) The receptor of Bacillus sphaericus binary toxin in Culex pipiens (Diptera: Culicidae) midgut: molecular cloning and expression. Insect Biochem Mol Biol 31:981-990.
Opota O, Gauthier NC, Doye A, Berry C Gounon P, Lemichez E, Pauron D (2011) Bacillus sphaericus binary toxin elicits host cell autophagy as a response to intoxication. PLoS One 6(2):e14682.
Tangsongcharoen C, Chomanee N, Promdonkoy B, Boonserm P (2015) Lysinibacillus sphaericus binary toxin induces apoptosis in susceptible Culex quinquefasciatus larvae. J Invertebr Pathol 128:57-63.

(Continued)

*Primary Examiner* — Rachael E Bredefeld
*Assistant Examiner* — Erinne R Dabkowski
(74) *Attorney, Agent, or Firm* — Brooks Kushman P.C.

(57) ABSTRACT

A chimeric protein comprising a cytolytic δ-endotoxin portion and a heterologous polypeptide portion is provided. Nucleic acids encoding the chimeric protein are also provided. In some cases, the chimeric protein can be expressed in parasporal inclusions of *Bacillus thuringiensis*. In certain cases, the cytolytic δ-endotoxin portion can include Cyt1Aa, and the heterologous portion can include an insecticidal polypeptide. The chimeric protein can be expressed in a suitable *B. thuringiensi* cell and purified as parasporal inclusions. Also provided is a method of controlling insects by exposing an insect to a chimerical insecticidal protein.

2 Claims, 4 Drawing Sheets
Specification includes a Sequence Listing.

(56) References Cited

OTHER PUBLICATIONS

Silva-Filha MH, Nielsen-LeRoux C, Charles J-F (1999) Identification of the receptor for Bacillus sphaericus crystal toxin in the brush border membrane of the mosquito Culex pipiens (Diptera: Culicidae). Insect Biochem. Mel Biol 29: 711-721.

Romão TP, de Melo Chalegre KD, Key S, Ayres CF, Fontes de Oliveira CM, de-Meld-Neto OP, Silva-Filha MH (2006) A second independent resistance mechanism to Bacillus sphaericus binary toxin targets its alpha-glucosidase receptor in Culex quinquefasciatus. FEBS J 273:1556-1568.

Wirth MC, Georghiou GP, Federici BA (1997) CytA enables CryIV endotoxins of Bacillus thuringiensis to overcome high levels of CryIV resistance in the mosquito, Culex quinquefasciatus. Proc Natl Aced Sci USA 94:10536-10540.

Wirth MC, Federici BA, Walton WE (2000) Cyt1A from Bacillus thuringiensis synergizes activity of Bacillus sphaericus against Aedes aegypti (Diptera: Culicidae). Appl Environ Microbiol 66:1093-1097.

Wirth MC, Walton WE, Federici BA (2000) Cyt1A from Bacillus thuringiensis restores toxicity of Bacillus sphaericus against resistant Culex quinquefasciatus (Diptera: Culicidae). J Med Entomol 37:401-407.

Wirth MC, Park H-W, Walton WE, Federici BA (2005) Cyt1A of Bacillus thuringiensis delays evolution of resistance to Cry11A in the mosquito Culex quinquefasciatus. Appl Environ Microbiol 71:185-189.

Park H-W, Bideshi DK, Wirth MC, Johnson JJ, Walton WE, Federici BA (2005) Recombinant larvicidal bacteria with markedly improved efficacy against Culex vectors of West Nile virus. Am J Trop Med Hyg 72:732-738.

Federici BA, Park H-W, Bideshi DK, Wirth MC, Johnson JJ, Sakano Y, Tang M (2007) Developing recombinant bacteria for control of mosquito larvae. J Am Mosq Control Assoc 23:164-175.

Wu D, Chang FN (1985) Synergism in mosquitocidal activity of 26 and 65 kDa proteins from *Bacillus thuringiensis* subsp. *israelensis* crystal. FEBS Lett 190:232-236.

Ibarra JE, Federici BA (1986) Isolation of a relatively nontoxic 65-kiiodalton protein inclusion from the parasporal boady of *Bacillus thuringiensis* subsp. *israelensis*. J Bacteriol 165:527-533.

Poncet S, Delecluse A, Klier Am Rapoport G (1995) Evaluation of synergistic interactions among the CryIVA, CryIVB and CryIVD toxic components of *B. thuringiensis* subsp. *israelensis* crystals. J Invertebr Pathol 66:131-135.

Cohen S, Albeck S, Ben-Dov E, Cahan R, Firer M, Zaritsky A, Dym O (2011) Cyt1Aa toxin: Crystal structure reveals implications for its membrane-perforating function. J Mol Biol 413:804-81.

Knowles BH, Ellar DJ (1987) Colloid-osmotic lysis is a general feature of the mechanism of action of Bacillus thuringiensis δ-endotoxins with different insect specificities, Biochim Biophys Acta 924:509-518.

Clark MA, Baumann P (1990) Deletion analysis of the 51-kilodalton protein of the Bacillus sphaericus 2362 binary mosquitocidal toxin: Construction of derivatives equivalent to the larva-processed toxin. J Bacteriol 172:6759-6763.

Darboux I. Pauchet Y, Castella c, Silva-Filha MH, Nielsen-LeRoux, Charles J-F, Pauron D. (2002) Loss of a membrane anchor as of the target receptor is a mechanism of bioinsecticides resistance, Proc Natl Acad Sci USA 99:5830-5835.

Park H-W. Bideshi DK, Federici BA (2003) Recombinant strain of Bacillus thuringiensis producing Cyt1A, Cry11B, and the Bacillus sphaericus binary toxin. Appl Environ Microbiol 69:1331-1334.

Pérez C, Fernandez LE, Sun J, Foich J, Gill SS, Soberón M, Bravo A (2005) *Bacillus thuringiensis* subsp. *israelensis* Cyt1Aa synergizes Cry11Aa toxin by functioning as a membrane-bound receptor. Proc Natl Aced Sci USA 102:18303-18308.

Federici BA, Park H-W, Bideshi DK, Wirth MC, Johnson JJ (2003) Recombinant bacteria for mosquito control. J Exp Biol 206: 3877-3885.

Hire RS, Hadapad AB, Dongre TK, Kumar V (2009) Purification and characterization of mosquitocidal Bacillus sphaericus protein. J Invertebr. Pathol 101:106-111.

Deist BR, Rausch MA, Fernandez-Luna MT, Adang, MJ, and Bonning BC (2014) Bt toxin modification for enhanced efficacy. Toxins 6:3005-3027.

Oei C, Hindley J, Berry C (1992) Binding of purified Bacillus sphaericus binary toxin and its deletion derivatives to Culex quinquefasciatus gut: elucidation of functional binding domains. J Gen Microbiol 138:1515-1526.

Boonserm P, Moonsom S, Boonchoy C, Promdonkoy B, Parthasarathy K, Torres J (2006) Association of the components of the binary toxin from Bacillus sphaericus in solution and with model lipid bilayers. Biochem Biophys Res Comm 342:1273-1278.

Limpanawat S, Promdonkoy B, Boonserm P (2009) The C-terminal domain of BinA is responsible for Bacillus sphaericus binary toxin BinA-BinB interaction. Curr Microbiol 59:509-513.

Srisucharitpanit K, Inchana P, Rungrod A, Promdonkoy B (2012) Expression and purification of the active soluble form of Bacillus sphaericus binary toxin for structural analysis. Prot Express Purific 82:368-372.

Kale A, Hire RS, Hadapad AB, D'Souza SF, Kumar V (2013) Interaction between mosquito-larvicidal *Lysinibacillus sphaericus* binary toxin components: Analysis of complex formation. Insect Biochem Mol Biol 43:1045-1054.

Hire RM, Sharma M, Hadapad AB, Kumar V (2014) An oligomeric complex of BinA/BinB is not formed in-situ in mosquito-larvicidal *Lysinibacillus sphaericus* ISPC-8, J Invertebr Pathol 122:44-47.

Srisucharitpanit K, Yao M, Promdonkoy B, Chimnarock S, Tanaka I, Boonserm P. (2014) Crystal structure of BinB: A receptor binding component of the binary toxin from Lysinibacillus sphaericus. Proteins 82:2703-2712.

Lekakarn H, Promdonkoy B, Boonserm, P. 2015. Interaction of Lysinibacillus sphaericus binary toxin with mosquito larval gut cells: Binding and internalization. J Invertebr Pathol 132:125-131.

Smith AW. Camara-Artigas A, Brune DC; Allen JP (2005) Implications of high-molecular weight oligomers of the binary toxin from Bacillus sphaericus. J Invertebr Pathol 88:7-33.

Hire RS, Hua G, Zhang Q, Mishra R, Adang AJ (2015) Anopheles gambiae Ag55 cell line as a model for Lysinibacillus sphaericus Bin toxin action. J Invertebr Pathol 132:105-110.

Wu D, Federici BA (1993) A 20-kilodalton protein preserves cell viability and promotes CytA crystal formation during sporulation in Bacillus thuringiensis. J Bacteriol 175:5276-80.

Bourgouin C, Delecluse A, de la Torre F, Szulmajster J (1990) Transfer of the toxin protein genes of Bacillus sphaericus into *Bacillus thuringiensis* subsp. *israelensis* and their expression. Appl Environ Microbiol 56:340-344.

Park H-W, Hice RH, Federici BA (2016) Effect of promoters and plasmid copy numbers on Cyt1A synthesis and crystal assembly in Bacillus thuringiensis. Curr Microbiol 72:33-40.

Sakano Y., Park H-W, Ge B. Bideshi DK, Federici BA (2016) Contributions of 5'-UTR and 3'-UTR cis elements to Cyt1Aa synthesis in *Bacillus thuringeinsis* subsp. *israelensis*. Submitted.

Berry C. O'Neil S, Ben-Dov E, Jones AF, Murphy L, Quail MA, Holden MT, Harris D, Zaritsky A, Parkhill J (2002) Complete sequence and organization of pBtoxis, the toxin-coding plasmid of *Bacillus thuringiensis* subsp. *israelensis*. Appl Environ Microbiol 68:5082-5095.

Baumann L, Broadwell AH, Baumann P (1988) Sequence analysis of the mosquitocidal genes encoding 51.4- and 41.9-kilodalton proteins from Bacillus sphaericus 2362 and 2297. J Bacteriol 170:2045-2050.

Bideshi DK, Waldrop G, Fernandez-Luna MT, Diaz-Mendoza M, Wirth MC, Johnson JJ, Park H-W, Federici BA (2013) Intermolecular interaction between Cry2Aa and Cyt1Aa and its effect on larvicidal activity against Culex quinquefasciatus. J Microbiol Biotechnol 23:1107-1115.

Park H-W, Bideshi DK, Johnson JJ, Federici BA (1999) Differential enhancement of Cry2A versus Cry11A yields in Bacillus thuringiensis by use of the cry3A STAB mRNA sequence. FEMS Microbiol Lett 181:319-327.

(56) References Cited

OTHER PUBLICATIONS

Bradford MM (1976) A rapid and sensitive method for the quantitation of microgram quantities of protein utilizing the principle of protein-dye binding. Anal Biochem 72:248-254.
Park H-W, Federici BA (2000) Domain I plays an important role in the crystallization of Cry3A in Bacillus thuringiensis. Mol Biotechnol 16:97-107.
Bideshi DK, et al.; International Congress on Invertebrate Pathology and Microbial Control and the 48th Annual Meeting of the Society for Invertebrate Pathology, Aug. 9-13, 2015; Abstract No. 156, presented Thursday, Aug. 13, 2015.
Charles J-F, Darboux I, Pauron D, Nielsen-Leroux C 2010 (first published 2005) Mosquitocidal Bacillus sphaericus: toxins, genetics, mode of action, use, and resistance mechanisms. In: Gilbert K L, ed. Elsevier Pergamon. pp. 207-231.
Yuan ZM, Zhang YM, Liu EY (2000) High-level field resistance to Bacillus sphaericus C3-41 in Culex quinquefasciatus from Southern China. Biocontrol Sci Technol 10:43-51.
Su T, Mulla MS (2004) Documantation of high-level Bacillus sphaericus 2362 resistance in field populations of Culex quinquefasciatus breeding in polluted water in Thailand. J Am Mosq Control Assoc 20:405-411.
Crickmore N, Bone EJ, Williams JA, Ellar DJ (1995) Contribution of the individual components of the ☐-endotoxin crystal to the mosquitocidal activity of *Bacillus thuringiensis* subsp. *israelensis*. FEMS Microbiol Lett 131:249-254.
Butko P, Huang F, Pusztai-Carey M, Surewicz WK (1996) Membrane permeabilization induced by cytolytic δ-endotoxin CytA from *Bacillus thuringiensis* var. *israelensis*. Biochemistry 35:11355-11360.
Butko P, Huang F, Pusztai-Carey M, Surewicz WK (1997) Interaction of the δ-endotoxin CytA from *Bacillus thuringiensis* var. *israelensis* with lipid membranes. Biochemistry 36:12862-12868.
Manceva SD, Pusztai-Carey M, Russo PS, Butko P (2005) A detergent-like mechanism of action of the cytolytic toxin Cyt1A from *Bacillus thuringiensis* var. *israelensis*. Biochemistry 44:589-597.
Tharad S, Iturri J, Moreno-Concerrado A, Mittendorfer M, Promdonkoy B, Krittanai C, Toca-Herra JL (2015). Effect of the concentration of cytolytic protein Cyt2Aa2 on the binding mechanism on lipid bilayers studied by OCM-D and AFM. Langmuir 31:10477-10483.
Rodriguez-Almazan C, Ruiz de Escudero I, Canton PE, Munoz-Garay C, Perez C, Gill SS, Soberón M, Bravo A (2010) The amino- and carboxyl-terminal fragments of the Bacillus thuringensis Cyt1Aa toxin have differential roles in toxin oligomerization and pore formation. Biochemistry 50:388-396.
Knowles BH (1994) Mechanism of action of Bacillus thuringiensis insecticidal δ-endotoxins. Adv Insect Physiol 24:275-30.
Al-yahyaeet SA, Ellar DJ (1995) Maximal toxicity of cloned CytA & endotoxin from *Bacillus thuringiensis* subsp. *israelensis* requires proteolytic processing from both the N- and C-termini, Microbiology 141:3141-3148.
Nicolas L, Lecroisey A, Charles JF (1990) Role of the gut proteinases from mosquito larvae in the mechanism of action and the specificity of the Bacillus sphaericus toxin. Can J Microbiol 36:804-807.
Davidson EW. (1979) Ultrastructure of midgut events in the pathogenesis of Bacillus sphaericus strain SSII-1 infections of Culex pipiens quinquefasciatus larvae. Can J Microbiol 25:178-184.
Wu D, Federici BA (1995) Improved production of the insecticidal CryIVD protein in Bacillus thuringiensis using cryIA (c) promoters to express the gene for an associated 20-kDa protein. Appl Micriobiol Biotech 42:697:702.
Lacey, LA, B. A. Federici, BA (1979) Pathogenesis and midgut histopathology of Bacillus thuringiensis in Simulium vittatum (Diptera: Simuliidae). J Invertebr Pathol 33:171-182.
Raymond M, Prato G, Ratsira D (1993) Probability analysis of mortality assays showing quantile response, version 3.3. Praxeme, Saint Georges D'argues, France.

\* cited by examiner

```
atggaaaatttaaatcattgtccattagaagatataaaggtaaatccatggaaaacccct
Met Glu Asn Leu Asn His Cys Pro Leu Glu Asp Ile Lys Val Asn Pro Trp Lys Thr Pro
caatcaacagcaagggttattacattacgtgttgaggatccaaatgaaatcaataatctt
Gln Ser Thr Ala Arg Val Ile Thr Leu Arg Val Glu Asp Pro Asn Glu Ile Asn Asn Leu
ctttctattaacgaaattgataatccgaattatatattgcaagcaattatgttagcaaat
Leu Ser Ile Asn Glu Ile Asp Asn Pro Asn Tyr Ile Leu Gln Ala Ile Met Leu Ala Asn
gcatttcaaaatgcattagttcccacttctacagatttggtgatgccctacgctttagt
Ala Phe Gln Asn Ala Leu Val Pro Thr Ser Thr Asp Phe Gly Asp Ala Leu Arg Phe Ser
atgccaaaaggtttagaaatcgcaaacacaattacaccgatgggtgctgtagtgagttat
Met Pro Lys Gly Leu Glu Ile Ala Asn Thr Ile Thr Pro Met Gly Ala Val Val Ser Tyr
gttgatcaaaatgtaactcaaacgaataaccaagtaagtgttatgattaataaagtctta
Val Asp Gln Asn Val Thr Gln Thr Asn Asn Gln Val Ser Val Met Ile Asn Lys Val Leu
gaagtgttaaaaactgtattaggagttgcattaagtggatctgtaatagatcaattaact
Glu Val Leu Lys Thr Val Leu Gly Val Ala Leu Ser Gly Ser Val Ile Asp Gln Leu Thr
gcagcagttacaaatacgtttacaaatttaaatactcaaaaaatgaagcatggattttc
Ala Ala Val Thr Asn Thr Phe Thr Asn Leu Asn Thr Gln Lys Asn Glu Ala Trp Ile Phe
tggggcaaggaaactgctaatcaaacaaattacacatacaatgtcctgtttgcaatccaa
Trp Gly Lys Glu Thr Ala Asn Gln Thr Asn Tyr Thr Tyr Asn Val Leu Phe Ala Ile Gln
aatgcccaaactggtggcgttatgtattgtgtaccagttggttttgaaattaaagtatca
Asn Ala Gln Thr Gly Gly Val Met Tyr Cys Val Pro Val Gly Phe Glu Ile Lys Val Ser
gcagtaaaggaacaagttttattttcacaattcaagattctgcgagctacaatgttaac
Ala Val Lys Glu Gln Val Leu Phe Phe Thr Ile Gln Asp Ser Ala Ser Tyr Asn Val Asn
atccaatctttgaaatttgcacaaccattagttagctcaagtcagtatccaattgcagat
Ile Gln Ser Leu Lys Phe Ala Gln Pro Leu Val Ser Ser Ser Gln Tyr Pro Ile Ala Asp
cttactagcgctattaatggaaccctctaa      (SEQ ID NO. 7)
Leu Thr Ser Ala Ile Asn Gly Thr Leu           (SEQ ID NO. 8)
```

FIG. 5

```
atgagaaatttggatttattgattctttataccacagaaggaaagtacattcgcgtt
Met Arg Asn Leu Asp Phe Ile Asp Ser Phe Ile Pro Thr Glu Gly Lys Tyr Ile Arg Val
atggattttataatagcgagtatcctttctgtatacatgcaccctcagcccctaatggg
Met Asp Phe Tyr Asn Ser Glu Tyr Pro Phe Cys Ile His Ala Pro Ser Ala Pro Asn Gly
gatatcatgacagaaatctgtagcagagaaataatcaatatttatttttttcctact
Asp Ile Met Thr Glu Ile Cys Ser Arg Glu Asn Asn Gln Tyr Phe Ile Phe Phe Pro Thr
gatgatggtcgagtaattattgcaaataggcataatgggtccgttttaccggagaagcc
Asp Asp Gly Arg Val Ile Ile Ala Asn Arg His Asn Gly Ser Val Phe Thr Gly Glu Ala
acaagtgtagtatcagatatctatactggtagcccattacagttttttagagaggtcaaa
Thr Ser Val Val Ser Asp Ile Tyr Thr Gly Ser Pro Leu Gln Phe Phe Arg Glu Val Lys
agaactatggcaacttattatttagcgatacaaaatcctgaatccgcaacagatgtgaga
Arg Thr Met Ala Thr Tyr Tyr Leu Ala Ile Gln Asn Pro Glu Ser Ala Thr Asp Val Arg
gctctagaaccgcattcccatgagctgccatctcgcctttattacactaacaatattgaa
Ala Leu Glu Pro His Ser His Glu Leu Pro Ser Arg Leu Tyr Tyr Thr Asn Asn Ile Glu
aataatagcaacatattaatttctaataaggaacaaatatatttaaccttgccttcactt
Asn Asn Ser Asn Ile Leu Ile Ser Asn Lys Glu Gln Ile Tyr Leu Thr Leu Pro Ser Leu
ccagaaaacgagcaatacctaaaactccagtattaagcggtatcgatgatataggacct
Pro Glu Asn Glu Gln Tyr Pro Lys Thr Pro Val Leu Ser Gly Ile Asp Asp Ile Gly Pro
aatcaatcagagaaatcaataataggaagtactcttatccatgtataatggtttcggat
Asn Gln Ser Glu Lys Ser Ile Ile Gly Ser Thr Leu Ile Pro Cys Ile Met Val Ser Asp
tttattagtttgggggagagaatgaaaaccactccatattatatgtaaagcacactcaa
Phe Ile Ser Leu Gly Glu Arg Met Lys Thr Thr Pro Tyr Tyr Tyr Val Lys His Thr Gln
tattggcaaagcatgtggtccgcgctctttccacccggctctaaagagacaaaactgag
Tyr Trp Gln Ser Met Trp Ser Ala Leu Phe Pro Pro Gly Ser Lys Glu Thr Lys Thr Glu
aaatcaggtatcactgacacttctcaaataagtatgactgacgggattaatgtttcaatc
Lys Ser Gly Ile Thr Asp Thr Ser Gln Ile Ser Met Thr Asp Gly Ile Asn Val Ser Ile
ggagcagatttcggattaaggtttggaaataaacgtttggaattaaggggggttcacc
Gly Ala Asp Phe Gly Leu Arg Phe Gly Asn Lys Thr Phe Gly Ile Lys Gly Gly Phe Thr
tatgatacaaagactcaaataactaataccteccaattgttaatagaaacaacttatact
Tyr Asp Thr Lys Thr Gln Ile Thr Asn Thr Ser Glu Leu Leu Ile Glu Thr Thr Lys Thr
agagaatacacaaatacagaaaattttcctgttagatatacaggctatgtttagcgtca
Arg Glu Tyr Thr Asn Thr Glu Asn Phe Pro Val Arg Tyr Thr Gly Tyr Val Leu Ala Ser
gaatttactttacatcgtagtgatggaactcaggttaatacgatcccatgggttgcttta
Glu Phe Thr Leu His Arg Ser Asp Gly Thr Gln Val Asn Thr Ile Pro Trp Val Ala Leu
aacgataactatacaacaatagcaagatatccacattttgcaagtgaacctttactagga
Asn Asp Asn Tyr Thr Thr Ile Ala Arg Tyr Pro His Phe Ala Ser Glu Pro Leu Leu Gly
aatacaaagattattacagatgatcaaaactaa          (SEQ ID NO. 9)
Asn Thr Lys Ile Ile Thr Asp Asp Gln Asn           (SEQ ID NO. 10)
```

FIG. 6

SEQUENCE LISTING

<160> NUMBER OF SEQ ID NOS: 10

<210> SEQ ID NO 1
<211> LENGTH: 12
<212> TYPE: DNA
<213> ORGANISM: Artificial Sequence
<220> FEATURE:
<223> OTHER INFORMATION: linker

<400> SEQUENCE: 1
aagcttggcg cc                                                          12

<210> SEQ ID NO 2
<211> LENGTH: 4
<212> TYPE: PRT
<213> ORGANISM: Artificial Sequence
<220> FEATURE:
<223> OTHER INFORMATION: linker

<400> SEQUENCE: 2

Lys Leu Gly Ala
1

<210> SEQ ID NO 3
<211> LENGTH: 37
<212> TYPE: DNA
<213> ORGANISM: Artificial Sequence
<220> FEATURE:
<223> OTHER INFORMATION: PCR primer

<400> SEQUENCE: 3
gggtaccatt tgataataat tgcaagttta aaatcat                                37

```
<210> SEQ ID NO 4
<211> LENGTH: 45
<212> TYPE: DNA
<213> ORGANISM: Artificial Sequence
<220> FEATURE:
<223> OTHER INFORMATION: PCR primer

<400> SEQUENCE: 4
gggcgccaag cttgagggtt ccattaatag cgctagtaag atctg            45

<210> SEQ ID NO 5
<211> LENGTH: 39
<212> TYPE: DNA
<213> ORGANISM: Artificial Sequence
<220> FEATURE:
<223> OTHER INFORMATION: PCR primer

<400> SEQUENCE: 5
aaagcttggc gccatgagaa atttggattt tattgattc                   39

<210> SEQ ID NO 6
<211> LENGTH: 33
<212> TYPE: DNA
<213> ORGANISM: Artificial Sequence
<220> FEATURE:
<223> OTHER INFORMATION: PCR primer

<400> SEQUENCE: 6
ggtcgacaaa caacaacagt ttacattcga gtg                         33

<210> SEQ ID NO 7
<211> LENGTH: 750
<212> TYPE: DNA
<213> ORGANISM: Bacillus thuringiensis

<400> SEQUENCE: 7
atggaaaatt taaatcattg tccattagaa gatataaagg taaatccatg gaaaacccct     60
caatcaacag caagggttat tacattacgt gttgaggatc caaatgaaat caataatctt    120 cttttctatta acgaaattga taatccgaat tatatattgc aagcaattat gttagcaaat    180
gcatttcaaa atgcattagt tcccacttct acagattttg gtgatgccct acgctttagt    240
atgccaaaag gtttagaaat cgcaaacaca attacaccga tgggtgctgt agtgagttat    300
gttgatcaaa atgtaactca aacgaataac caagtaagtg ttatgattaa taaagtctta    360
gaagtgttaa aaactgtatt aggagttgca ttaagtggat ctgtaataga tcaattaact    420
gcagcagtta caaatacgtt tacaaattta aatactcaaa aaaatgaagc atggattttc    480
tggggcaagg aaactgctaa tcaaacaaat tacacataca atgtcctgtt tgcaatccaa    540
aatgcccaaa ctggtggcgt tatgtattgt gtaccagttg gttttgaaat taaagtatca    600
gcagtaaagg aacaagtttt atttttcaca attcaagatt ctgcgagcta caatgttaac    660
atccaatctt tgaaatttgc acaaccatta gttagctcaa gtcagtatcc aattgcagat    720
cttactagcg ctattaatgg aaccctctaa                                     750

<210> SEQ ID NO 8
<211> LENGTH: 249
<212> TYPE: PRT
<213> ORGANISM: Bacillus thuringiensis
```

<400> SEQUENCE: 8

```
Met Glu Asn Leu Asn His Cys Pro Leu Glu Asp Ile Lys Val Asn Pro
1               5                   10                  15
Trp Lys Thr Pro Gln Ser Thr Ala Arg Val Ile Thr Leu Arg Val Glu
            20                  25                  30

Asp Pro Asn Glu Ile Asn Asn Leu Leu Ser Ile Asn Glu Ile Asp Asn
        35                  40                  45
Pro Asn Tyr Ile Leu Gln Ala Ile Met Leu Ala Asn Ala Phe Gln Asn
    50                  55                  60
Ala Leu Val Pro Thr Ser Thr Asp Phe Gly Asp Ala Leu Arg Phe Ser
65                  70                  75                  80
Met Pro Lys Gly Leu Glu Ile Ala Asn Thr Ile Thr Pro Met Gly Ala
                85                  90                  95
Val Val Ser Tyr Val Asp Gln Asn Val Thr Gln Thr Asn Asn Gln Val
            100                 105                 110
Ser Val Met Ile Asn Lys Val Leu Glu Val Leu Lys Thr Val Leu Gly
        115                 120                 125
Val Ala Leu Ser Gly Ser Val Ile Asp Gln Leu Thr Ala Ala Val Thr
    130                 135                 140

Asn Thr Phe Thr Asn Leu Asn Thr Gln Lys Asn Glu Ala Trp Ile Phe
145                 150                 155                 160
Trp Gly Lys Glu Thr Ala Asn Gln Thr Asn Tyr Thr Tyr Asn Val Leu
                165                 170                 175
Phe Ala Ile Gln Asn Ala Gln Thr Gly Gly Val Met Tyr Cys Val Pro
            180                 185                 190
Val Gly Phe Glu Ile Lys Val Ser Ala Val Lys Glu Gln Val Leu Phe
        195                 200                 205
Phe Thr Ile Gln Asp Ser Ala Ser Tyr Asn Val Asn Ile Gln Ser Leu
    210                 215                 220
Lys Phe Ala Gln Pro Leu Val Ser Ser Ser Gln Tyr Pro Ile Ala Asp
225                 230                 235                 240
Leu Thr Ser Ala Ile Asn Gly Thr Leu
                245
```

<210> SEQ ID NO 9
<211> LENGTH: 1113
<212> TYPE: DNA
<213> ORGANISM: Lysinibacillus sphaericus

<400> SEQUENCE: 9

```
atgagaaatt tggattttat tgattctttt atacccacag aaggaaagta cattcgcgtt      60
atggattttt ataatagcga gtatcctttc tgtatacatg caccctcagc ccctaatggg     120
gatatcatga cagaaatctg tagcagagaa aataatcaat attttatttt ttttcctact     180
gatgatggtc gagtaattat tgcaaatagg cataatgggt ccgtttttac cggagaagcc     240
acaagtgtag tatcagatat ctatactggt agcccattac agtttttttag agaggtcaaa     300 agaactatgg caacttatta tttagcgata caaaatcctg aatccgcaac agatgtgaga     360
gctctagaac cgcattccca tgagctgcca tctcgccttt attacactaa caatattgaa     420
aataatagca acatattaat ttctaataag gaacaaatat atttaacctt gccttcactt     480
ccagaaaacg agcaataccc taaaactcca gtattaagcg gtatcgatga tataggacct     540
aatcaatcag agaaatcaat aataggaagt actcttatcc catgtataat ggtttcggat     600
tttattagtt tgggggagag aatgaaaacc actccatatt attatgtaaa gcacactcaa     660
```

```
tattggcaaa gcatgtggtc cgcgctcttt ccacccggct ctaaagagac aaaaactgag    720
aaatcaggta tcactgacac ttctcaaata agtatgactg acgggattaa tgtttcaatc    780
ggagcagatt tcggattaag gtttggaaat aaaacgtttg gaattaaggg ggggttcacc    840
tatgatacaa agactcaaat aactaatacc tcccaattgt taatagaaac aacttatact    900
agagaataca caaatacaga aaattttcct gttagatata caggctatgt tttagcgtca    960
gaatttactt tacatcgtag tgatggaact caggttaata cgatcccatg ggttgcttta   1020
aacgataact atacaacaat agcaagatat ccacattttg caagtgaacc tttactagga   1080
aatacaaaga ttattacaga tgatcaaaac taa                                1113

<210> SEQ ID NO 10
<211> LENGTH: 370
<212> TYPE: PRT
<213> ORGANISM: Lysinibacillus sphaericus

<400> SEQUENCE: 10

Met Arg Asn Leu Asp Phe Ile Asp Ser Phe Ile Pro Thr Glu Gly Lys
1               5                   10                  15

Tyr Ile Arg Val Met Asp Phe Tyr Asn Ser Glu Tyr Pro Phe Cys Ile
            20                  25                  30

His Ala Pro Ser Ala Pro Asn Gly Asp Ile Met Thr Glu Ile Cys Ser
        35                  40                  45

Arg Glu Asn Asn Gln Tyr Phe Ile Phe Phe Pro Thr Asp Asp Gly Arg
    50                  55                  60

Val Ile Ile Ala Asn Arg His Asn Gly Ser Val Phe Thr Gly Glu Ala
65                  70                  75                  80

Thr Ser Val Val Ser Asp Ile Tyr Thr Gly Ser Pro Leu Gln Phe Phe
                85                  90                  95

Arg Glu Val Lys Arg Thr Met Ala Thr Tyr Tyr Leu Ala Ile Gln Asn
            100                 105                 110

Pro Glu Ser Ala Thr Asp Val Arg Ala Leu Glu Pro His Ser His Glu
        115                 120                 125

Leu Pro Ser Arg Leu Tyr Tyr Thr Asn Asn Ile Glu Asn Asn Ser Asn
    130                 135                 140

Ile Leu Ile Ser Asn Lys Glu Gln Ile Tyr Leu Thr Leu Pro Ser Leu
145                 150                 155                 160

Pro Glu Asn Glu Gln Tyr Pro Lys Thr Pro Val Leu Ser Gly Ile Asp
                165                 170                 175

Asp Ile Gly Pro Asn Gln Ser Glu Lys Ser Ile Ile Gly Ser Thr Leu
            180                 185                 190

Ile Pro Cys Ile Met Val Ser Asp Phe Ile Ser Leu Gly Glu Arg Met
        195                 200                 205

Lys Thr Thr Pro Tyr Tyr Tyr Val Lys His Thr Gln Tyr Trp Gln Ser
    210                 215                 220

Met Trp Ser Ala Leu Phe Pro Pro Gly Ser Lys Glu Thr Lys Thr Glu
225                 230                 235                 240

Lys Ser Gly Ile Thr Asp Thr Ser Gln Ile Ser Met Thr Asp Gly Ile
                245                 250                 255

Asn Val Ser Ile Gly Ala Asp Phe Gly Leu Arg Phe Gly Asn Lys Thr
            260                 265                 270

Phe Gly Ile Lys Gly Gly Phe Thr Tyr Asp Thr Lys Thr Gln Ile Thr
        275                 280                 285
```

-continued

```
Asn Thr Ser Gln Leu Leu Ile Glu Thr Thr Tyr Thr Arg Glu Tyr Thr
    290             295             300
Asn Thr Glu Asn Phe Pro Val Arg Tyr Thr Gly Tyr Val Leu Ala Ser
305             310             315             320
Glu Phe Thr Leu His Arg Ser Asp Gly Thr Gln Val Asn Thr Ile Pro
            325             330             335
Trp Val Ala Leu Asn Asp Asn Tyr Thr Thr Ile Ala Arg Tyr Pro His
        340             345             350
Phe Ala Ser Glu Pro Leu Leu Gly Asn Thr Lys Ile Ile Thr Asp Asp
    355             360             365
Gln Asn
    370
```

USE OF CYT1AA AS BROAD SPECTRUM TARGETING DOMAIN FOR INSECTICIDAL PROTEINS WITH BASIC RESEARCH AND BIOTECHNOLOGY APPLICATIONS

CROSS-REFERENCE TO RELATED APPLICATIONS

This application claims the benefit of Provisional Patent Application No. 62/360,096, filed on Jul. 8, 2016, which is incorporated by reference herein.

STATEMENT REGARDING FEDERALLY SPONSORED RESEARCH OR DEVELOPMENT

This invention was made with Government support under Grant No. RO1 AI045817 from the National Institutes of Health. The Government has certain rights in this invention.

REFERENCE TO SEQUENCE LISTING

A Sequence Listing is submitted electronically via EFS-Web as an ASCII formatted text file with the name "1279602SeqList"; the file was created on Jul. 10, 2017, is 9.27 kilobytes in size, and is incorporated herein by reference in its entirety.

BACKGROUND

Field of the Invention

The invention relates to chimeric proteins and insecticidal compositions.

Related Art

Two naturally occurring mosquitocidal bacilli, *Bacillus thuringiensis* subsp. *israelensis* (Bti) and *Lysinibacillus sphaericus* (Ls), are the active ingredients of commercial larvicides used for controlling nuisance and vector mosquitoes. Bti's high insecticidal activity is due to synergistic interactions among its four major proteins (Cry4Aa, Cry4Ba, Cry11Aa, and Cyt1Aa), whereas Ls's principal toxicity is caused by the binary mosquitocidal crystal, Bin, containing BinA, a toxin domain, and BinB a midgut-binding domain. Although used in many countries for over three decades, resistance to Bti is very rare. However, Bin resistance levels greater than 20,000-fold have occurred where Ls has been used intensively for mosquito control. Bti's Cyt1Aa is a lipophilic protein of low toxicity that binds to midgut microvilli causing lesions that allow other molecules to enter midgut epithelial cells. In previous studies it was shown that Cyt1Aa delays the evolution of resistance to Bti Cry proteins and Ls Bin, and can overcome resistance to these when selected for in the laboratory.

SUMMARY

The protein Cyt1Aa was assayed as a broad-spectrum targeting domain by fusing it to BinA. Here it is shown that the Cyt1Aa-BinA chimera accumulates in a parasporal body in 4Q7, an acrystalliferous strain of Bti, and has remarkably high toxicity to larvae of major mosquito vectors, namely, *Anopheles gambiae, An. stephensi*, Bin-sensitive and Bin-resistant strains of *Culex quinquifasciatus*, and *Aedes aegypti*, the latter which is not normally sensitive to Ls Bin. These results show that the Cyt1Aa-BinA chimera, and other similar constructs, will have high efficacy against most major mosquito disease vectors, including the primary mosquitoes species that vector malaria, yellow fever, filariasis, and newly emerging viruses such as the Zika virus. Cyt1Aa may prove useful as a targeting protein for other insecticidal proteins used to control dipteran vectors and possibly for dipteran and non-dipteran agricultural pests. Moreover, Cyt1Aa could be used to facilitate occlusion of other proteins or peptides of interest, particularly pharmaceuticals, that by themselves are unable to form inclusions or to be crystallized.

In one aspect, a chimeric protein comprising a cytolytic δ-endotoxin portion and a heterologous polypeptide portion is provided. In some embodiments, the chimeric protein can be expressed in parasporal inclusions of *Bacillus thuringiensis*. In particular embodiments: a) the cytolytic δ-endotoxin portion can comprise Cyt1Aa or a biologically active fragment or variant thereof; b) the cytolytic δ-endotoxin portion can comprise at least the mature form of Cyt1Aa; c) the cytolytic δ-endotoxin portion can comprise at least amino acids 1-249, or 1-234, or 30-249, or 30-234, or 31-249, or 31-234, of the Cyt1A1 amino acid sequence (SEQ ID NO. 8); d) the heterologous polypeptide portion can comprise a heterologous polypeptide; e) the heterologous polypeptide can be an insecticidal polypeptide; f) the insecticidal polypeptide can be BinA, mosquitocidal toxin 1 (Mtx1), Cry1 1Ba or other Cry proteins of *Bacillus thuringiensis*, or vegetative insecticidal proteins (VIPs) of *Bacillus thuringiensis*, or an insecticidally active fragment or variant thereof, or a combination thereof; g) the heterologous polypeptide portion can comprise two or more insecticidal polypeptides, which can be the same or different insecticidal polypeptides; h) the C-terminal end or N-terminal end of the cytolytic δ-endotoxin portion can be fused to the heterologous portion; for example, the C-terminus or N-terminus of Cyt1Aa can be fused to an insecticidal polypeptide; i) the *Bacillus thuringiensis* can be *Bacillus thuringiensis* subsp. *israelensis*; or j) any combination of a)-i).

In another aspect, a nucleic acid comprising a sequence encoding the chimeric protein is provided. In some embodiments: a) the cytolytic δ-endotoxin portion of the chimeric protein can comprise Cyt1Aa or a biologically active fragment or variant thereof; b) a nucleic acid comprising a sequence complementary to the sequence of the chimeric protein is provided; c) the nucleic acid can be part of a vector; d) a host cell containing the vector is provided; e) the host cell can be a bacterial cell of *E. coli, B. thuringiensis*, or other species of bacilli or other bacteria such as *Lysinibacillus sphaericus, Anabaena* sp., *Synechococcus* sp. so long as the host cell also contains the 20-kD accessory protein that prevents Cyt1Aa from interacting with the plasma membrane of the host cell (63, 64); or f) any combination of a)-e).

In a further aspect, a method of controlling a dipteran insect is provided. The method includes exposing the midgut of the insect to an insecticidally effective amount of an insecticidal chimeric protein, which can be in the form of parasporal inclusions containing the insecticidal chimeric protein. In some embodiments: a) the cytolytic δ-endotoxin portion of the chimeric protein can comprise Cyt1Aa or a biologically active fragment or variant thereof; b) the insect can be an *Anopheles, Aedes*, or *Culex* mosquito, or another mosquito vector, or a vector in the suborder Nematocera, including black flies (e.g., *Simulium* species) and biting midges (such as *Culicoides* species); c) the insect can be an insect that is resistant to a spinosad insecticide; d) the insect is further exposed to one or more different insecticidal chimeric proteins; or e) any combination of a)-d).

BRIEF DESCRIPTION OF THE DRAWINGS

For a more complete understanding of the present invention, reference is now made to the following descriptions taken in conjunction with the accompanying drawings, in which:

FIG. 3 is a picture of SDS-PAGE demonstrating Cyt1Aa-BinA is susceptible to proteolytic cleavage by trypsin. Cyt1Aa was used as a control. Purified parasporal body samples were solubilized in 50 mM NaOH, supernatants collected and neutralized with HCl, and digested with the enzyme at 28° C. Untreated samples, 1.5 hr (lane 1), and trypsin-treated samples, 0.5 hr (lane 2) and 1.5 hr (lane 3). M, protein molecular mass standards; kDa, kilodaltons.

FIG. 4 is a panel showing midgut histopathology caused by Cyt1Aa-BinA chimera in fourth instars of *Culex quinquefasciatus* 8 hours post-treatment at the LC95 concentration. (4A and 4B) Control midgut epithelium (4A, 100×; 4B, 400×). (4C and 4D) Midgut epithelium of a treated larva. Note the vacuoles in cells designated by arrows in 4D that have sloughed from the midgut basement membrane (4C, 100×; 4D, 600×). The central circular area in 4A is the food column (fc) surrounded by the peritrophic membrane.

FIG. 5 provides the nucleotide and amino acid sequence of Cyt1Aa.

FIG. 6 provides the nucleotide and amino acid sequence of BinA.

DETAILED DESCRIPTION

Figure 1:
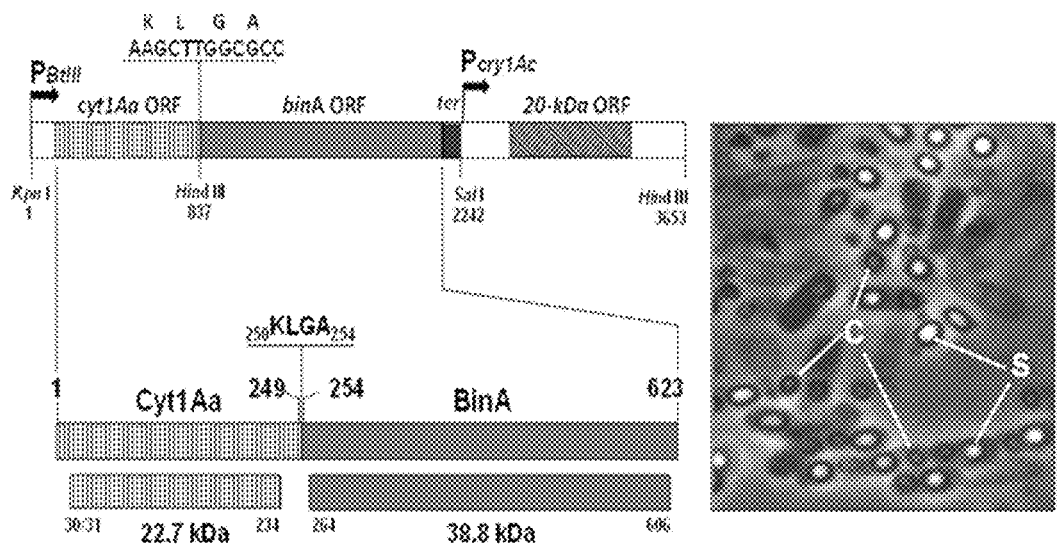
FIG. 1 is a panel showing parasporal inclusions of a chimeric Cyt1Aa-BinA synthesized by acrystalliferous *Bacillus thuringiensis* subsp. *israelensis* 4Q7. (1A) Schematic of the cyt1Aa-binA gene fusion. A 0.84-kbp fragment containing the cyt1Aa gene BtIII promoter ($P_{BtIII}$) and cyt1Aa open reading frame (ORF) was cloned in frame with a 1.4 kbp fragment harboring the binA ORF flanked by its native transcription terminator (ter). The nucleotide sequences at the fusion site (underlined; AAGCTTG-GCGCC (SEQ ID NO. 1)) and the coded amino acids (KLGA, lysine-leucine-glycine-alanine; SEQ ID NO. 2) are shown above the HindIII site, as are the positions of applicable restriction sites and the 20-kDa-like chaperone protein gene under control of the cryIAc gene promoter ($P_{cryIAc}$) used for cloning in pBU4 to generate the expression vector pBU-cyt1Aa-binA. The Cyt1Aa-BinA protoxin is composed of 623 amino acids and has a molecular mass of 69.6 kDa; the predicted proteolytically active forms of Cyt1Aa (22.7 kDa) and BinA (38.8 kDa) are shown. (1B) Micrograph (×1000) of 4Q7/pBU-cyt1Aa-binA grown for 48 hr showing sporulated cells with endospore (s) and parasporal inclusions (c); free spores and inclusions are also poresent, as is typical after lysis of *B. thuringiensis* cells.

In one aspect, a chimeric protein comprising a cytolytic δ-endotoxin portion and a heterologous polypeptide portion is provided. In some embodiments, the cytolytic δ-endotoxin portion includes Cyt1Aa or a biologically active fragment or variant thereof.

The nucleotide and amino acid sequences of Cyt1Aa are shown in FIG. 5. Cyt1Aa is a 249 amino acid polypeptide. The N- and C-termini of this protoxin is cleaved at amino acids 30/31 and 234 upon solubilization and activation by proteases. Cyt1Aa adopts a typical cytolysin fold containing a β-sheet held by two surrounding α-helical layers. Based on the Cyt1Aa structure, the toxicity of Cyt1Aa and other nonrelated proteins, all sharing a cytolysin fold, is correlated with their ability to undergo conformational changes that are necessary prior to their membrane insertion and perforation. This fold allows the α-helical layers to swing away, exposing the β-sheet to insert into the membrane. The identification of a putative lipid binding pocket between the β-sheet and the helical layer of Cyt1Aa supports this mechanism (38). There are three Cyt classes with subtypes—Cyt1Aa, Cyt1Ab, Cyt1Ba, Cyt1Ca, Cyt1Da, Cyt2Aa, Cyt2Ba, Cyt2Bb, Cyt2Bc, Cyt2Ca and Cyt3Aa—known from *B. thuringiensis*. In some embodiments, instead of Cyt1Aa, the cytolytic δ-endotoxin portion can include any of these other Cyt classes or subtypes, or fragments or variants thereof.

A heterologous polypeptide is a protein, polypeptide or peptide, other than the cytolytic δ-endotoxin contained in the cytolytic δ-endotoxin portion of the chimeric protein, or other than a polypeptide or peptide derived from the cytolytic δ-endotoxin. For example, when Cyt1Aa is the cytolytic δ-endotoxin, the heterologous polypeptide is a protein, polypeptide or peptide other than Cyt1Aa or a polypeptide or peptide derived from Cyt1Aa. Examples of heterologous polypeptides include, but are not limited to, non-insecticidal proteins, polypeptides and peptides, and insecticidal proteins, polypeptides or peptides such as, but not limited to, the insecticidal polypeptide BinA, mosquitocidal toxin 1 (Mtx1), Cry11Ba and other Cry proteins of *Bacillus thuringiensis*, and vegetative insecticidal proteins (VIPs) of *Bacillus thuringiensis*, and insecticidally active fragments or variants of thereof.

In some embodiments, the heterologous polypeptide is an insecticidal polypeptide. The insecticidal polypeptide can be a complete form of an insecticidal protein, polypeptide or peptide, or can be the part of the insecticidal protein, polypeptide or peptide responsible for insecticidal activity. Insecticidal activity is the ability to kill or paralyze an insect, to inhibit development, growth, feeding, pupation, or reproduction of an insect, or any combination thereof. An insecticidally effective amount of an insecticidal composition is an amount that provides insecticidal activity against the target insect. Chimeric proteins having insecticidal activity are considered to be insecticidal chimeric proteins.

The insecticidal polypeptide can be BinA, mosquitocidal toxin 1 (Mtx1), Cry11Ba and other Cry proteins of *Bacillus thuringiensis*, and vegetative insecticidal proteins (VIPs) of *Bacillus thuringiensis*, or an insecticidally active fragment or variant thereof, or any other insecticidal protein or peptide that acts at the cell surface or inside the cell. For example, Mtx1 is a soluble mosquitocidal toxin produced by *L. sphaericus* whereas Cry11Ba is a crystal-forming mosquitocidal toxin produced by *B. thuringiensis* subsp. *jegathesan*, and VIPs are lepidopteran-specific protoxin produced during vegetative growth of various strains of *Bacillus thuringiensis*. In some embodiments, the insecticidal polypeptide can be an insecticidally active portion of any of these insecticidal proteins or peptides.

The nucleotide and amino acid sequences of BinA are shown in FIG. 6. The BinA protein is the toxic domain of the binary toxin (Bin) of *Lysinibacillus sphaericus*. Bin is composed of two proteins of molecular masses 42 kDa (BinA) and 51 kDa (BinB) that co-crystallize to form a single parasporal inclusion that is encapsulated with the spore during late stage of bacterial growth. When activated in mosquito larval midgut, BinB functions as the receptor binding domain, and BinB recruits activated BinA, the toxin domain, into the target cell where the activated BinA/BinB, or BinA alone, induces larval death by degradation of the midgut epithelia. Generally, BinA/BinB and BinA are highly toxic to all known *Culex* species, and many important anopheline species, such as the key malaria vector in Africa, *Anopheles gambiae*. In addition, many *Aedes* species are sensitive to Bin, although these species are not as significant as the *Aedes aegypti* vector.

The nucleotide and protein sequences for Cyt1Aa and BinA can be obtained from: GenBank Accession number X03182 for Cyt1Aa, GenBank Accession number M20390 for BinA and BinB, GenBank Accession number Q03988 for Mtx1, and GenBank Accession number Q45730 for Cry1 1Ba, HM536938.2 for VIP3A, JQ855505.1 for VIP1, and JQ855506.1 for VIP2, all incorporated by reference herein. In addition, the GenBank Accession numbers for various Cyt polypeptides include: X03182, X04338, Y00135, M35968, AL731825, ABC17640, and KF152888 (for Cyt1Aa); X98793 (for Cyt1Ab); U37196 (for Cyt1Ba); AL731825 (for Cyt1Ca); HQ113115 and JN226105 (for Cyt1Da); Z14147, AF472606, EU835185, and AEG19547 (for Cyt2Aa); U52043, AF020789, AF022884, AF022885, AF022886, AF034926, AF215645, AF215646, AL731825, ACX54358, ACX54359, ACX54360, FJ205865, FJ205866, and JF283552 (for Cyt2Ba); U82519 (for Cyt2Bb); CAC80987 (for Cyt2Bc); AAK50455 for Cyt2Ca; and HM596591 (for Cyt3Aa), all incorporated by reference herein.

A nucleic acid can be a single stranded or double stranded oligo or polymer of RNA or DNA. In some embodiments, modified nucleotide backbones such as, but not limited to, phosphorothioates, phosphorodithioates, methyl and other alkyl phosphonates (e.g., 3'-alkylene phosphonates and chiral phosphonates), phosphinates, phosphoramidates (e.g., 3'-amino phosphoramidate and aminoalkylphosphoramidates), thionophosphoramidates, thionoalkylphosphonates, thionoalkyl phosphotriesters, or boranophosphates, can be incorporated.

A polypeptide is a polymer of amino acid residues joined by peptide bonds, whether produced naturally or synthetically. Polypeptides of less than about 10 amino acid residues are commonly referred to as "peptides."

In some embodiments, the cytolytic δ-endotoxin (such as Cyt1Aa) can be a naturally occurring or experimentally derived variant of the cytolytic δ-endotoxin. Similarly, the insecticidal polypeptide can be a naturally occurring or experimentally derived variant of an insecticidal protein, polypeptide or peptide. A substitutional variant of a protein, polypeptide or peptide contains an exchange of one amino acid for another at one or more sites within the protein, polypeptide or peptide. The substitution is typically a conservative substitution involving the exchange of amino acids that are similar in shape and/or charge. A deletion variant lacks one or more residues of the native protein, polypeptide or peptide. An insertion mutant or variant includes the addition of one or more amino acids at a non-terminal point in the protein, polypeptide or peptide. Variants can have about 80% or more identity, about 85% or more identity, or about 90% or more identity, about 95% or more identity, about 98% or more identify, or about 100% identity, to the naturally occurring protein, polypeptide or peptide sequence. A sequence comparison can be performed, for example, using Clustal Omega, MUSCLE, MView, or MAFFT sequence comparison programs. In comparing sequences, a segment of comparison between one protein and another may be about 100% of the amino acids of the length being compared, or about 95%, about 85%, or about 80% of the amino acids of the length being compared. The length of comparison may be at least about 20, 30, 40, 50, 55, 60, 65, 70, or 75 amino acids, or more. The variants may conserve particular physicochemical or functional features as the prevailing natural sequence, while other variants may have modified combinations of structural and functional features.

A specialized kind of insertional variant is the fusion protein. This molecule generally has all, a substantial portion, or the active portion of the native molecule, linked at the N- or C-terminus, to all or a portion of a second polypeptide.

In some embodiments, a variant or fragment of a cytolytic δ-endotoxin (such as Cyt1Aa) can be a biologically active variant or fragment of the cytolytic δ-endotoxin. A biologically active variant or fragment of the cytolytic δ-endotoxin, for example, can bind to insect midgut microvilli, or form microvillar membrane lesions in the insect microvilli, or a combination thereof.

A chimeric protein can be encoded in a vector. A vector is a carrier nucleic acid molecule into which a nucleic acid sequence can be inserted for introduction into a cell where it can be replicated. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Molecular Cloning: a Laboratory Manual: 3rd edition, Sambrook and Russell, 2001, Cold Spring Harbor Laboratory Press). A vector can encode polypeptide sequences such as a tag or targeting molecule; for example, vectors can encode a stretch of histidines, or can be used to generate glutathione S-transferase (GST) soluble fusion proteins. An expression vector contains a nucleic acid sequence encoding a polypeptide, and a variety of control sequences which are necessary for the transcription and/or translation of an operably linked coding sequence in a particular host organism.

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and can be obtained through the American Type Culture Collection (ATCC), which is an organization that serves as an archive for living cultures and genetic materials. An appropriate host can be determined by one of skill in the art based on the vector backbone and the desired result. Examples of eukaryotic host cells for replication and/or expression of a vector include HeLa, NIH3T3, Jurkat, 293, Cos, CHO, Saos, and PC12.

In certain embodiments, a protein, polypeptide, or peptide may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide. Parasporal bodies can be purified or isolated, for example, by ultracentrifugation.

Compositions containing bacteria, spores, parasporal inclusions, and/or chimeric proteins, including insecticidal or pesticidal compositions, can be formulated as solutions, emulsions, suspensions, emulsifiable concentrates, spray powders, pastes, soluble powders, dusting agents, granules, foams, pastes, tablets, aerosols, natural and synthetic materials impregnated with active compounds, and microcapsules. Such compositions may be obtained by the addition of a surface active agent, such as a dispersing agent, emulsifying agent or wetting agent, or an inert carrier for handling and application. Non-ionic, anionic, amphoteric, or cationic dispersing and emulsifying agents that may be employed include, but are not limited to, the condensation products of alkylene oxides with phenol and organic acids, alkyl aryl sulfonates, complex ether alcohols, quaternary ammonium compounds, and the like. Inert materials include, but are not limited to, inorganic minerals such as phyllosilicates, carbonates, sulfates, phosphates; organic materials such as sugar, starches, or cyclodextrins; or botanical materials such as powdered corncobs, rice hulls, walnut shells, cornmeal, pelleted grains, and cellulosic fibers.

In some embodiments, the insecticidal compositions may be employed alone or in the form of mixtures with such solid and/or liquid dispersible carrier vehicles and/or other known compatible active agents such as other pesticides, or pediculicides, acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

The composition can be applied to an area, such as a field, garden, yard, outdoor area, or the like. An insecticidal composition can be applied to a plant, which can include ornamentals and agricultural crop plants. In other embodiments, an insecticidal composition can be applied to a structure or part of a structure, such as a house, greenhouse, storage shed, or the like.

As described herein, a chimeric gene (cyt1Aa-binA) was constructed that contained (i) a sequence harboring the BtIII promoter and open reading frame of the cyt1Aa gene of *Bacillus thuringiensis* subsp. *israelensis* (Bti) fused in frame with (ii) a sequence coding for the toxin domain (BinA) and transcription terminator of the binary toxin gene (bin) of *Lysinibacillus sphaericus* strain 2362 (Ls). The construct was cloned in the shuttle vector, pBU4-20 kDa, which contained the 20-kDa chaperone protein gene of Bti, to generate the recombinant plasmid, pBU-BtIIICyt42. An acrystalliferous strain of Bti (4Q7) transformed with pBU-BtIIICyt42 produced stable parasporal inclusions containing the chimera, Cyt1Aa-BinA (69.6 kDa). Bioassays using spore/Cyt1Aa-BinA inclusions of the recombinant 4Q7 strain demonstrated that the chimera was remarkably toxic to *Anopheles gambiae, Anopheles stephensi, Anopheles quadrimaculatus*, Bin-sensitive and Bin-resistant strains of *Culex quinquifasciatus*, and *Aedes aegypti*, the latter which is not normally sensitive to Ls Bin.

Novel Features And Advantages Of Embodiments Of The Invention
1. Cyt1Aa can be used as a broad spectrum targeting domain for BinA and likely other proteins.
2. The Cyt1Aa-BinA chimera occurs as a stable inclusion in *Bacillus thuringiensis*.
3. The Cyt1Aa-BinA component shows levels of toxicity comparable to Bti, which harbors a much more complex parasporal body composed of at least 4 crystalline inclusions (Cry4Aa, Cry4Ba, Cry 11Aa, Cyt1Aa) against Bin-sensitive and Bin-resistant *Culex quinquefasciatus, Anopheles gambiae*, and *Anopheles stephensi* and *Anopheles quadrimaculatus*.
4. The Cyt1Aa-BinA chimera expands the target range of BinA to include *Aedes aegypti* and likely other mosquito species that do not contain midgut docking proteins to which the Bin endotoxin of *Lysinibacillus sphaericus* binds.
5. When ingested by mosquito larvae as a unit, it is expected that the presence of the Cyt1Aa component of the Cyt1Aa-BinA chimera will (i) synergize BinA's activity by enabling the latter protein to enter midgut cells, and (ii) delay or prevent the evolution of resistance to BinA in natural mosquito populations.
6. Cyt1Aa can be used as a general domain to facilitate occlusion and targeting of other insecticidal toxins for use against vector and pest insects that have developed resistance to these toxins.
7. It is expected that Cyt1Aa can be used as a general domain to target a wide variety of prokaryote and eukaryote proteins that normally do not form inclusions following hyperexpression of their corresponding genes in heterologous systems.
8. The Cyt1A-BinA chimera can overcome resistance to the class of chemical insecticides known as spinosads.

The present invention may be better understood by referring to the accompanying examples, which are intended for illustration purposes only and should not in any sense be construed as limiting the scope of the invention.

EXAMPLE 1

Abstract

Two bacilli, *Bacillus thuringiensis* subsp. *israelensis* (Bti) and *Lysinibacillus sphaericus* (Ls), are used as commercial larvicides for mosquito control. Bti's efficacy is due to synergistic interactions among four parasporal body proteins (Cry4Aa, Cry4Ba, Cry1 1Aa, and Cyt1Aa), whereas Ls's toxicity is caused by Bin, a heterodimer consisting of BinA, a toxin domain, and BinB, a midgut-binding domain. Although used for over three decades, resistance to Bti is rare, whereas Bin resistance greater than 20,000-fold has been reported in vector mosquito populations. Bti's Cyt1Aa binds directly to midgut microvillar lipids but has low toxicity. In previous studies we showed Cyt1Aa delays resistance to Bti's Cry proteins and Ls Bin, and overcomes resistance to these. Thus, Cyt1Aa was used as a broad-spectrum targeting domain by fusing it to BinA. Here it is shows that this Cyt1Aa-BinA chimera accumulates in the parasporal body of a crystal-minus Bt strain, which has remarkably high toxicity to larvae of major vector mosquitoes including *Anopheles gambiae, An. stephensi*, Bin-sensitive and Bin-resistant *Culex quinquifasciatus*, and Bin-tolerant *Aedes aegypti*, the latter an important Dengue and Zika virus vector, indicating this fusion may be useful for vector control. In addition, the results suggest Cyt1Aa enables BinA to enter midgut cells and be highly toxic without BinB or conformational changes required through interactions with microvillar membrane lipids. These results show that once inside the cytoplasm of midgut epithelial cells, BinA alone can likely target what is probably an organelle membrane, thereby advancing knowledge of Bin's mode of action.

Two bacilli, *Bacillus thuringiensis* subsp. *israelensis* (Bti) and *Lysinibacillus sphaericus* (Ls) are the active ingredients of bacterial insecticides used to control larvae of nuisance and vector mosquitoes. Cyt1A is a membrane lipid-binding protein that permits the Cry proteins of Bti to enter microvilli yielding high efficacy.

Mosquitoes transmit a wide variety of pathogens that cause debilitating diseases including the viruses that cause Dengue, West Nile, Zika and Yellow Fever, nematodes responsible for River Blindness and filariasis, and protozoans causing various malarias. Over half the human population lives in areas where these mosquito-vectored pathogens are endemic, with the principal vectors being species of *Aedes, Anopheles*, and *Culex* mosquitoes. Recent data from the World Health Organization show that more than 3 billion people are at risk of malaria alone, with an estimated 198 million cases and greater than 550,000 deaths annually, most of the latter being children who die under the age of 5, making malaria the leading cause of morbidity and mortality worldwide (1). The incidence of Dengue and Yellow Fever is also high, with respectively, 50-100 million and 200,000 cases occurring yearly (2, 3).

Over the past 75 years, synthetic pesticides such as DDT, organophosphates, and pyrethroids have been used successfully to control mosquitoes. However, detrimental residual effects of these chemicals on ecosystems combined with the rapid emergence of resistance in field populations of insects (4) led to the development of alternative control strategies that incorporate two basic components: high-specificity toward target pests and short-term stability of pesticides in ecosystems where applied. Toward this end *Bacillus thuringiensis* subsp. *israelensis* (Bti) and *Lysinibacillus sphaericus* (Ls), naturally occurring bacteria that have these characteristics, have been used extensively over the past three decades to control mosquito larvae (5-8). Their larvicidal activity is due primarily to protein toxins that accumulate as one or more crystalline inclusions in the cell during sporulation.

Bti produces four major proteins, three Cry (crystal) protoxins (Cry4Aa, Cry4Ba, Cry1 1Aa) and one Cyt (cytolytic) protoxin (Cyt1Aa), which assemble in a single parasporal body released following cell lysis. When ingested, these protoxins dissolve in the alkaline larval midgut, are proteolytically activated, bind to microvillar receptors, and form lesions that destroy midgut cells leading to larval death (5, 7, 8). Cyt1Aa, a highly lipophilic protein of 27.5 kDa (9, 10). binds to midgut microvilli, synergizing Bti's mosquitocidal Cry proteins and delays the evolution of resistance to these and Ls Bin toxins (5, 11, 12). Cyt1Aa is thought to act by binding to the plasmalemma of midgut microvilli forming pores or lipid faults (13). The four mosquitocidal proteins of Bti's parasporal body, delivered as a single unit per os, are a potent natural larvicide to which significant resistance has not been observed in field populations of mosquitoes, due primarily to the presence of Cyt1Aa.

The Ls binary parasporal body differs from Bti's in that it is composed of the so-called binary toxin (Bin) a heterodimer of two related propeptides, BinA, a 42-kDa toxin, and BinB a non-toxic 51-kDa protein (6, 14, 15), that binds to a midgut receptor, the first identified being a glycosylphosphatidylinositol (GPI)-anchored α-glucosidase (16). Moreover, although like Bti's parasporal body, the dimer dissolves from the Bin crystal in the midgut lumen and both proteins are activated, their mode of action differs significantly. Specifically, after binding to its midgut receptor BinB initiates endocytosis of the BinA/BinB dimer, and once within the cytoplasm, a complex series of events occur characterized by formation of large vacuoles, apparently caused by BinA, resulting in autophagy in a mammalian cell model system (17) or apoptosis (18) in mosquito midgut cells. The latter results in exfoliation of the midgut and larval death. At $LC_{90}$ levels, Bti mortality peaks at 24 hours post-treatment, whereas in Ls, owing to the endocytosis process, maximum mortality does not occur until 48 hours post-treatment (19). Unlike Bti, high levels of resistance to Ls, as the BinA/BinB complex is in essence a single toxin, has been observed frequently where this larvicide has been applied intensively (20, 21). This resistance is due to mutations in BinB's receptors, which comprise a single class of GPI-anchored α-glucosidases (15, 22, 23).

Although Bti and Ls are safe and effective larvicides, it was demonstrated that recombinant Bti strains containing various combinations of mosquitocidal Cry proteins, Cyt1Aa, and Bin are much more potent than wild type strains of Bti and Bs, and delay or avoid the development of resistance (24-29). While these recombinant strains are examples of how bacterial insecticides can be improved significantly, existing knowledge of Cyt, Cry, and Bin proteins suggests that other novel combinations can be constructed which may be of high efficacy and have the capacity to avoid resistance or overcome it in mosquito populations where it evolves. For instance, as BinA's mode of action is (i) different from that of Cry proteins, (ii) requires BinB to bind to a very specific type of receptor, and (iii) Cyt binds to the microvillar lipids throughout the mosquito midgut epithelium, i.e., Cyt does not require a specific protein receptor, it was decided to determine whether this lipid-binding, lesion-forming protein could serve as a general targeting domain for a mosquitocidal toxin like BinA. To test this possibility, a chimera, Cyt1Aa-BinA (69.6 kDa), was constructed consisting of Cyt1Aa fused to BinA, and then this protein was evaluated for stable synthesis in 4Q7, an acrystalliferous strain of Bti, and for its efficacy against representative larvae of vector mosquitoes belonging to the genera *Aedes, Anopheles*, and *Culex*. Here it is demonstrated that this chimera forms a stable parasporal inclusion in 4Q7 and is highly efficacious against *Anopheles gambiae*, An. *stephensi*, and *Culex quinquefasciatus*, in the latter case, both Bin-sensitive and Bin-resistant strains. Moreover and importantly, this chimera expanded the target spectrum of BinA to include *Aedes aegypti*, a species with very low sensitivity to Ls Bin (6). The results suggest that Cyt1Aa and other general binding domains may be useful in extending the target spectrum and efficacy of a variety of insecticidal proteins to many vectors and possibly even agricultural pests.

Results

The Cyt1Aa-BinA construct included amino acids 1-249 of Cty1Aa and amino acids 1-369 of BinA.

Figures 3, 4:
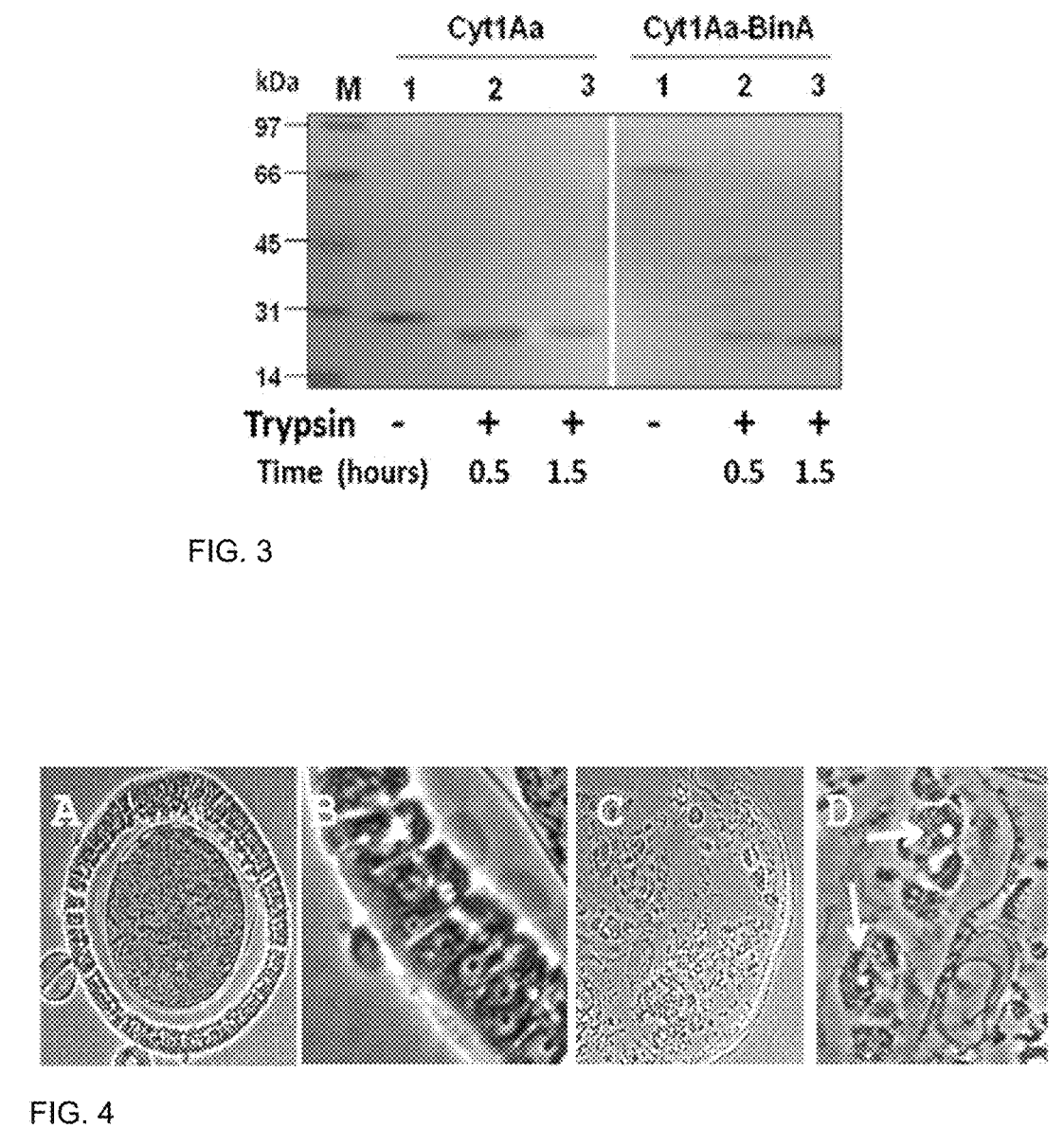

The Bti 4Q7 strain constructed to synthesize Cyt1Aa-BinA (FIG. 1A) produced spores and parasporal bodies within 24-36 hr of incubation in NBG broth or on Nutrient agar (FIG. 1B). The parasporal bodies were released from fully lysed cells, and when kept in NBG broth or Nutrient agar remained stable for at least eight weeks at 4° C., as determined by microscopy and SDS-PAGE, making them suitable for bioassays. To determine whether the parasporal bodies contained the Cyt1Aa-BinA chimera, they were separated from spores using a sucrose gradient and analyzed by SDS-PAGE and Western blot analyses. A single protein band migrating at ~70 kDa, the predicted mass of Cyt1Aa-BinA, was observed, and this protein reacted with the anti-Cyt1Aa and anti-BinA antibodies (respectively, FIGS. 2A and 2B). When subjected to digestion with trypsin, the Cyt1Aa-BinA chimera yielded fragments consistent with normal cleavage products of Cyt1A and BinA (FIG. 3).

Against all larvae, bioassays of the Cyt1Aa strain showed only negligible toxicity, with $LC_{50}$s ranging from 4,219-47,370 ng/ml and $LC_{95}$s from 13,722-155,050 ng/ml (Table 1). Bti 4Q5, a strain which only produces its four major toxins (Cry4Aa, Cry4Ba, Cry11Aa and Cyt1Aa), was the most potent ($LC_{50}$s 3.6-7.1 ng/ml, $LC_{95}$s from 18.5-88 ng/ml). Ls 2362 was active against *Cx. quinquefasciatus* S-LAB, and *An. gambiae* and *An. stephensi*, but not against *Ae. aegypti* and *Cx. quinquefasciatus* BS-R, a strain selected for high levels of resistance to Bin; the $LC_{50}$s and $LC_{95}$s of Ls 2362 were >1,000,000 ng/ml. The Cyt1Aa-BinA chimeric strain, however, was highly toxic to larvae of species belonging to three major genera of disease vectors, *Culex*, *Aedes* and *Anopheles*, with $LC_{50}$s ranging from 9.2 to 61.9 ng/ml, and $LC_{95}$s from 30 to 271 ng/ml (Table 1). Toxicity of the chimera was high by 24 hours post-treatment (Table 1), which typically only occurs by 48 hours when Ls 2362 is tested against larvae (Table 2).

TABLE 1

Toxicity of *Bacillus thuringiensis* subsp. *israelensis* (Bti) and *Lysinibacillus sphaericus* (Ls) strains against $4^{th}$-instars of *Culex quinquefasciatus*, *Aedes aegypti*, *Anopheles gambiae* and *Anopheles stephensi*[a]

| Bacterial Strain (Toxins produced) | $LC_{50}$ (Fiducial Limits) | $RT^d$-$LC_{50}$ | $LC_{95}$ (Fiducial Limits) | $RT^d$-$LC_{95}$ | Slope |
|---|---|---|---|---|---|
| *Culex quinquefasciatus* S-Lab | | | | | |
| Bti 4Q7/pWF45 (Cyt1Aa) | 47,370.1 (35,629.5-59,705.4) | 6,671 | 155,050.3 (114,040.8-260,168.4) | 1,914.2 | 3.2 ± 0.5 |
| Ls 2362 (BinAB) | 181.4 (118.1-296.3) | 25.6 | 7,569.4 (3,009.6-33,192.5) | 93.5 | 1.0 ± 0.1 |
| Bti 4Q7/cyt1Aa-binA (Cyt1Aa-BinA chimera) | 9.2 (7.2-12.1) | 1.3 | 30.5 (2.02-.71.2) | 0.4 | 3.2 ± 0.6 |
| Bti 4Q5 (Cry4A, Cry4B, Cry11A, Cyt1A) | 7.1 (2.6-18.6) | 1.0 | 81.0 (16.7-427.3) | 1.0 | 1.6 ± 0.4 |
| *Culex quinquefasciatus* BS-R[b] | | | | | |
| Bti 4Q7/pWF45 (Cyt1Aa) | 27,022.4 (20,523.2-35,262.4) | 5,630 | 100,175.2 (70,685.6-169,448.0) | 4,595.2 | 2.9 ± 0.4 |
| Ls 2362 (BinAB) | >1,000,000[c] | >208,333 | >1,000,000[c] | >45,872 | — |
| Bti 4Q7/cyt1Aa-binA (Cyt1Aa-BinA chimera) | 10.2 (2.6-41.4) | 2.1 | 42.0 (2.2-1,214.9) | 1.9 | 2.7 ± 1.0 |
| Bti 4Q5 (Cry4A, Cry4B, Cry11A, Cyt1A) | 4.8 (3.5-6.3) | 1.0 | 21.8 (14.4-45.3) | 1.0 | 2.5 ± 0.4 |
| *Aedes aegypti* | | | | | |
| Bti 4Q7/pWF45 (Cyt1Aa) | 4,218.7 (2,997.1-5,709.8) | 1,172 | 22,764.9 (14,634.9-48,334.1) | 84 | 2.3 ± 0.4 |
| Ls 2362 (BinAB) | >1,000,000 | >277,778 | >1,000,000[c] | >3,689 | — |
| Bti 4Q7/cyt1Aa-binA (Cyt1Aa-BinA chimera) | 61.9 (46.7-80.1) | 17.2 | 271.1 (185.1-513.4) | 14.7 | 2.6 ± 0.4 |
| Bti 4Q5 (Cry4A, Cry4B, Cry11A, Cyt1A) | 3.6 (2.5-4.8) | 1.0 | 18.5 (11.9-39.6) | 1.0 | 2.3 ± 0.4 |
| *Anopheles gambiae* | | | | | |
| Bti 4Q7/pWF45 (Cyt1Aa) | 46,557.3 (13,980.9-137,613.6) | 1,757 | 129,978.8 (25,520.6-923,387.1) | 1,465.4 | 3.7 ± 1.4 |
| Ls 2362 (BinAB) | 201.2 (154.6-260.4) | 7.6 | 1,150.9 (760.7-2,206.5) | 13 | 2.2 ± 0.3 |
| Bti 4Q7/cyt1Aa-binA (Cyt1Aa-BinA chimera) | 23.0 (17.6-30.0) | 0.9 | 80.9 (57.4-135.4) | 0.9 | 3.0 ± 0.4 |
| Bti 4Q5 (Cry4A, Cry4B, Cry11A, Cyt1A) | 26.5 (20.2-34.3) | 1.0 | 88.7 (63.9-144.8) | 1.0 | 3.1 ± 0.4 |
| *Anopheles stephensi* | | | | | |
| Bti 4Q7/pWF45 (Cyt1Aa) | 7,779.5 (6,758.9-9,028.8) | 526 | 13,722.2 (11,212.0-20,809.5) | 195 | 6.7 ± 1.3 |
| Ls 2362 (BinAB) | 707.5 (620.3-808.5) | 48 | 1,179.2 (992.0-1,618.5) | 17 | 7.4 ± 1.3 |
| Bti 4Q7/cyt1Aa-binA (Cyt1Aa-BinA chimera) | 28.9 (22.0-37.2) | 1.9 | 93.1 (67.8-149.8) | 1.3 | 3.2 ± 0.4 |
| Bti 4Q5 (Cry4A, Cry4B, Cry11A, Cyt1A) | 14.8 (11.1-19.8) | 1.0 | 70.4 (46.8-133.2) | 1.0 | 2.4 ± 0.3 |

[a] 24 hr-mortality, ng/ml
[b] Laboratory strain selected for high-level resistance to the binary toxin (Bin) of Ls 2362
[c] No mortality at 1 mg/ml
[d] Relative toxic values of recombinant Bti strains and Ls 2362 against mosquito larvae when compared to strain Bti 4Q5

TABLE 2

Toxicity of *Bacillus thuringiensis* subsp. *israelensis* Cyt1Aa-BinA chimeric strain or the *Lysinibacillus sphaericus* (Ls) wild type strain against $4^{th}$-instars of *Culex quinquefasciatus* (S-Lab strain) at 24 versus 48 hr

| Bacterial Strain | $LC_{50}$ (Fiducial Limits)[a] | $LC_{95}$ (Fiducial Limits)[a] | Slope |
|---|---|---|---|
| 24 hours | | | |
| Ls 2362 (BinAB) | 218.7 (158.5-308.0) | 2,548.5 (1,396.8-6.667.3) | 1.5 ± 0.2 |
| Bti 4Q7/cyt1Aa-binA (Cyt1Aa-BinA chimera) | 6.5 (3.3-13.0) | 38.5 (11.0-174.6) | 2.1 ± 0.5 |

TABLE 2-continued

Toxicity of *Bacillus thuringiensis* subsp. *israelensis* Cyt1Aa-BinA chimeric strain or the *Lysinibacillus sphaericus* (Ls) wild type strain against 4th-instars of *Culex quinquefasciatus* (S-Lab strain) at 24 versus 48 hr

| Bacterial Strain | $LC_{50}$ (Fiducial Limits)[a] | $LC_{95}$ (Fiducial Limits)[a] | Slope |
|---|---|---|---|
| 48 hours | | | |
| Ls 2362 (BinAB) | 19.5 (14.7-25.9) | 90.5 (61.5-160.3) | 2.5 ± 0.3 |
| Bti 4Q7/cyt1Aa-binA (Cyt1Aa-BinA chimera) | 5.8 (2.7-12.5) | 31.0 (7.6-151.8) | 2.3 ± 0.6 |

[a]ng/ml

Interestingly, with regard to both $LC_{50}$s and $LC_{95}$s, the relative toxicities of the Cyt1Aa-BinA chimera and Bti (strain 4Q5) with the wild type parasporal body against all larvae assayed, with the exception of *Ae. aegypti*, were not significantly different, as they ranged from 0.4-2.1, even against the BinA/BinB-resistant *Cx. quinquefasciatus* BS-R strain (Table 1). Against the anopheline species, although fiducial limits of $LC_{50}$s of the Cyt1Aa-BinA protein (23.0 ng/ml) and Bti 4Q5 (26.5 ng/ml) against *An. gambiae* overlapped, those of Cyt1Aa-BinA (28.9 ng/ml) and Bti 4Q5 (14.8 ng/ml) against *An. stephensi* did not. However, their $LC_{95}$s completely overlapped against both species indicating that the Cyt1Aa-BinA fusion protein alone was as effective as the wild-type Bti 4Q5.

Perhaps most interesting are the $LC_{50}$s and $LC_{95}$s toxicities observed for Cyt1Aa-BinA against *Ae. aegypti*, respectively, 61.9 ng/ml and 271.1 ng/ml, when compared to Ls 2362 (>1,000,000 ng/ml), i.e., the chimera was >16,155 and >3689 more toxic than Ls 2362. Although not as toxic to *Ae. aegypti* as Bti (4Q5) with the wild type parasporal body ($LC_{50}$=3.6 ng/ml, $LC_{95}$=18.5 ng/ml), these results demonstrate that the Cyt1Aa-BinA chimera extended the target spectrum of Ls BinA.

Preliminary histological studies of treated versus control larvae showed that the midgut epithelium was completely destroyed in moribund and dead larvae by eight hours post-treatment at the $LC_{95}$ level (FIG. 4). Most midgut cells had sloughed from the basement membrane and had lysed. Those that still had a recognizable cellular structure lacked microvilli and had one or two large vacuoles in the cytoplasm, characteristics of the cytopathology resulting from Ls Bin intoxication.

Discussion

In previous studies the inventors demonstrated that Cyt1Aa synergizes the activity of Ls Bin against *Ae. aegypti*, and overcomes resistance to this protein in *Cx. quinquefasciatus* (25, 26). Larvae of *Ae. aegypti* lack a Bin receptor, as do those of *Cx. quinquefasciatus* resistant to Bin (19, 23). In other studies, it has been shown that Cyt1Aa synergizes mosquitocidal Cry proteins (30-33), and can overcome resistance to mosquitocidal proteins such as Cry11Aa (27). As noted above, the mode of action of Cyt1Aa is not well understood, but a variety of evidence suggests that this protein binds to and permealizes the microvillar plasmalemma (34-37). This suggested Cyt1Aa might be used to create lesions in mosquito midgut microvillar membranes that would enable endotoxins and certain other molecules that act inside cells to enter and exert toxicity. Virtually all data show that BinA acts inside cells (6, 14-19), not at the microvillar surface, and thus this protein seemed an ideal candidate to test this hypothesis. Therefore, the inventors' objectives were to determine whether Cyt1Aa when fused with BinA would have two functions, (i) form a stable parasporal body containing the Cyt1Aa-BinA chimera, and if so, (ii) enable BinA to gain access to its intracellular target site in the presence or absence of its BinB-specific α-glucosidase receptor through the action of Cyt1Aa's membrane lesion-forming activity. The results presented here show that the Cyt1Aa-BinA chimera was synthesized as a stable parasporal body (FIG. 1), and was highly toxic not only to mosquitoes known to be sensitive to Ls Bin, but to tolerant species such as *Ae. aegypti*, and to those resistant to this protein, such as the BS-R strain of *Cx. quinquefasciatus* (Table 1).

How Cyt1Aa enabled BinA to enter the cell in vivo was not determined, but the two prevailing models proposed— "pore-former" versus "detergent"—provided a basis for the inventors design of the Cyt1Aa-BinA chimera. The pore-forming model suggests that monomeric Cyt1Aa binds to the plasmalemma and undergoes conformational changes where β-strands in its C-terminal half are inserted into the membrane while its N-terminal half, composed primarily of α-helices, is exposed on the extracytoplasmic face of the membrane (36-39). Oligomerization of Cyt1Aa molecules on the membrane results in formation of β-barrel pores that disrupt osmotic balance leading to eventual colloid-osmotic lysis of the cell (40-42). In the "detergent-like" model, Cyt1Aa aggregates on the surface of cells causing nonspecific defects in membrane integrity followed by leakage of intracellular molecules that results in cell lysis (13, 34-37). Most data support the latter model. However, regardless of the model, the chimera used Cyt1Aa to transport BinA to the mosquito midgut lumen where the former molecule would cause microvillar membranes lesions that enable the latter protein toxin to enter the midgut epithelial cells. The Cyt1Aa-BinA chimera fused the protoxins of these two proteins, each which contains its native proteolytic cleavage sites (FIG. 1B, FIG. 3) for activation (43-45). Thus, shortly after entering the midgut, it is likely that the fused protoxins are activated, i.e., proteolytically cleaved, after which the Cyt1Aa and BinA molecules separate from one another and act independently, the former causing lesions in the membrane enabling BinA to quickly enter the cell to reach its target site. For this reason, as when Cyt1Aa is combined with Ls 2362 against tolerant larvae like *Ae. aegypti*, which lack a Bin receptor (6, 25), or *Cx. quinquefasciatus* BSR larvae resistant to Bin (23, 25, 46), mortality is high at 24 hours (Tables 1), whereas in wild type larvae of this species Bin mortality peaks at 48 hours post-treatment (Table 2). Similar results were obtained using recombinant strains of Bti that produced Cyt1Aa, Bin, and Cry 1 1B (47).

Although not wishing to be bound by theory, the inventors favor a mode of action for the chimera in which Cyt1Aa and BinA function independently, because it is much less likely after activation by proteolytic cleavage that BinA and Cyt1Aa reassociate, with the latter then binding BinA to the microvillar membrane, which apparently occurs in vivo with Cry 1 1Aa and Cyt1Aa (48). The highly specific packaging of Cyt1Aa and Cry11Aa in Bti suggest these have a long evolutionary relationship, during which their binding was selected for because it resulted in high toxicity. No such evolutionary association is known between Cyt1Aa and BinA, thus the evidence suggests they do not bind to one another (49). For this reason the inventors consider Cyt1A's role in the chimera as a targeting domain rather than a receptor or binding domain. With bacterial endotoxins, such as Cry proteins, receptor typically refers to GPI-anchored or other proteins that are normal constituents of midgut cells and microvilli.

The high toxicity to *Ae. aegypti* ($LC_{50}$=69.1 ng/ml, $LC_{95}$=271.1 ng/ml, Table 1) was unexpected because this species is not a target of Bin, and Cyt1Aa's effect is also negligible. However, Wirth et al. (25) showed that when *L. sphaericus* technical powder was combined with purified Cyt1Aa crystals at a 10:1 ratio an increase in toxicity to *Ae. aegypti* was observed, with $LC_{50}$ and $LC_{95}$ values of 3,800 ng/ml and 31,500 ng/ml, and synergism factors of 2.1 and 8.6, respectively. Therefore, when compared with these results, at the $LC_{50}$ and $LC_{95}$ values, the chimera, with a 1:1 ratio of Cyt1Aa:BinA, increased toxicity to *Ae. aegypti* by, respectively, 55-fold and 116.2-fold. The marked differences in $LC_{50}$ and $LC_{95}$ values between the two studies cannot be compared directly due to variations in toxin constructs used in the bioassays. Unlike *Culex* and certain *Anopheles* species, *Ae. aegypti* lacks receptors that bind BinB (6, 25), or if present, BinB binds with low affinity. Nevertheless, the toxicity the inventors obtained with the chimera demonstrates that the intracellular target for BinA is present in all four species.

It was speculated above that Cyt1Aa facilitates intracellular localization of BinA through lesions formed in the microvillar plasmalemma, or much less likely, through its role as a substitute binding domain for BinA. Regardless of the mechanism, the inventors' study supports the use of Cyt1Aa as a non-specific targeting domain that allows cellular import of proteins that act inside the cell. Moreover, whereas the inventors' focus has been on increasing net synthesis of insecticidal proteins in Bti and Ls strains to increase toxicity (28, 49), non-specific or specific targeting of these proteins to their sites of action is potentially of greater importance. For example, Nicholas et al. (14) were able to produce amorphous parasporal inclusions of BinA and BinB separately in Bt SPL407. Bioassays against *Culex pipiens* demonstrated that BinB, the receptor-binding domain, was not toxic whereas the $LC_{50}$ of BinA at 48 h was 300 ng/ml, compared to 1.8 ng/ml when Bin, i.e., BinA/BinB, was used against fourth instars. Hire et al. (50) were also able to produce BinA alone, and obtained an $LC_{50}$ of 66.9 ng/ml, but against third instars of *Cx. quinquefasciatus*, which are only about 20% the wet weight of fourth instars, making their values and those of Nicolas et al. (14) difficult to compare directly. These values are similar to what the inventors observed in *Cx. quinquefasciatus* (26) using the spore/Bin complex combined with Cyt1Aa, and in this study with the Cyt1Aa-BinA chimera (Table 1). In the latter case, it is estimated that BinA constitutes only about 10% of the dry weight of spore/parasporal complex, indicating that its activated peptide once inside the cell is one of the most potent mosquitocidal toxins known, if not the most toxic.

Strains producing inclusions composed of the Cyt1Aa-BinA fusion can have applied value, as bioassays against other dipteran vectors can show. Commercial products in which wild type Bti and Ls strains are combined, are commercially available. However, the activity of wild type strains in these products is not nearly as efficacious as recombinant bacteria that combine the endotoxins of these two species in single strains (29). Moreover, the present study provides a foundation for exploring alternative approaches for developing even more novel recombinants that target vector species of mosquitoes and perhaps even economically significant dipteran, lepidopteran and coleopteran pests of agriculture, for which other types of recombinant proteins show considerable promise (51).

Figure 2:
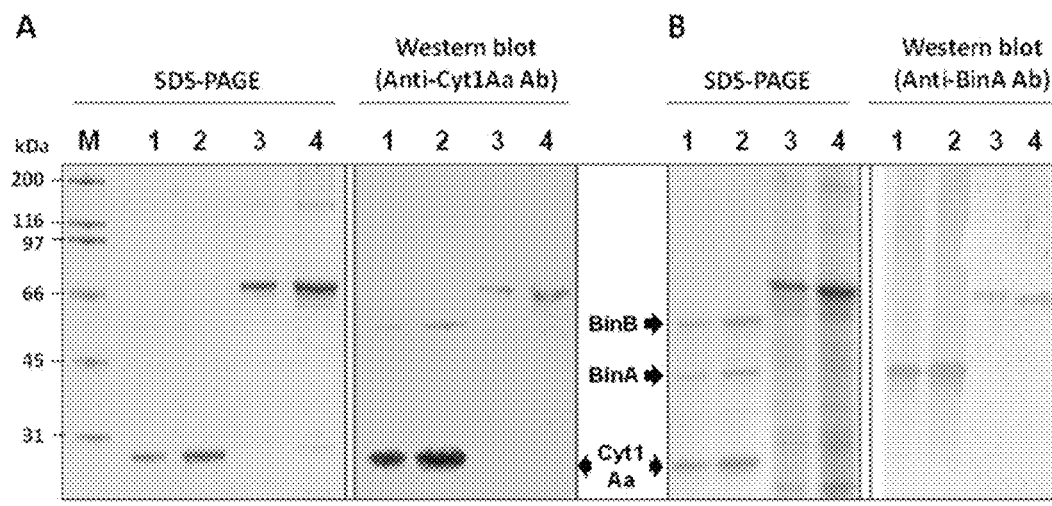
FIG. 2 is a panel showing the protein profile and antigenicity of a Cyt1Aa-BinA chimera. Inclusion bodies were purified from *Bacillus thuringiensis* subsp. *israelensis* 4Q7 strains producing, (2A) Cyt1Aa (4Q7/pWF45; lanes 1, 2) and Cyt1A-BinA (4Q7/pBU-cyt1Aa-binA; lanes 3, 4), and (2B) Cyt1Aa and BinAB (4Q7/45S1; lanes 1, 2) and Cyt1A-BinA (4Q7/pBU-cyt1A-binA; lanes 3, 4). Inclusions were solubilized and fractionated by SDS-PAGE in a 10% gel and electroblotted for Western analysis using rabbit anti-Cyt1Aa and anti-BinA antibodies (Ab). Lanes 1, 2, and 3, 4, respectively, 0.75 µg and 1.5 µg of protein; molecular masses: Cyt1Aa, 27.2 kDa; BinA, 42 kDa; BinB, 52 kDa; and Cyt1Aa-BinA 69.6 kDa. M, protein molecular mass standards; kDa, kilodaltons.

Aside from any potential vector control applications, the Cyt1Aa-BinA chimera could prove useful for clarifying the properties of Bin and its mode of action that result in mosquito death. The literature on these topics is full of variable, disparate, and often contradictory results. Whereas Bin's cytopathology of intoxication has been well described (17, 18, 52, 53), the mode of action at the molecular level remains unknown. Midgut cell death has been attributed recently to apoptosis (18) but autophagy without death occurs in a mammalian cell system (17). Evidence is strong that BinA is the principal toxin component and inclusions of this protein without BinB are toxic (14, 15), but a relatively recent report found that highly pure BinA alone is not toxic (56). In most studies over the past decade it is assumed that after Bin enters the midgut lumen and dissolves, BinA and BinB dissociate, are then activated, and then reassociate to form an activated dimer or tetramer (2BinA+2BinB). However, strong evidence for the initial dissociation in vivo or tetramer formation is lacking (17, 18, 54-60; see Sriscucharitpanit et al. [59] FIG. 6 for a schematic summary of key events). In fact many of these studies cite Smith et al. (61) regarding the tetramer, but Hire et al. (58) have shown recently that the Ls protein complex studied by the former group was a spore coat protein complex, not the Bin toxin. In numerous other studies it has been suggested that reassociation of BinA and BinB may be required for important conformational changes essential to both molecules so that Bin can bind receptors, interact with membrane lipids for additional structural alterations, and induce its endocytosis (among others see 54, 55, 57, 59). Whereas the inventors do not question these results under the conditions tested, the in vivo results reported here provide strong evidence that once BinA is activated it is highly toxic without requiring BinB for conformational changes, nor does it likely require interactions with microvillar membrane lipids for toxicity (FIG. 2, FIG. 3, Table 1). This suggests that BinA's hydrophobic domains may target this toxin to an intracellular organelle system, such as the endoplasmic reticulum (6), rather than forming pores in the microvillar membrane.

Previously using toxins labeled with fluorescent dyes the inventors demonstrated that Cyt1A enabled the BinAB dimer to enter epithelial cells along the entire midgut (49), not just the gastric caecae and posterior midgut (52, 53), in Bin-resistant *Cx. quinquefasciatus* larvae, which lacks a BinB receptor (26). It was assumed that the activated dimer entered the cells without binding to microvilli, regardless of whether BinA and BinB disassociated and reassociated. However, whether they had to disassociate within the cell for BinA to be active is not known. Hire et al. (62) recently reported the development of a cell line from *Anopheles gambiae* that is sensitive to Bin. This cell line and the inventors' chimera may be useful for clarifying the underlying mechanism by which Bin, and especially BinA kills cells.

EXAMPLE 2

Materials and Methods

Bacterial strains, culture media, and DNA extraction. The DH5α strain of *Escherichia coli* (Invitrogen) was used for cloning and amplifying plasmid DNA. The strains of crystalliferous *B. thuringiensis* subsp. *israelensis* (Bti) 4Q5, acrystalliferous Bti 4Q7, and *L. sphaericus* (Ls) 2363 were obtained from the *Bacillus* Genetic Stock Center (Ohio State University, Columbus, Ohio). Erythromycin-resistant recombinants 4Q7/pWF45 and 4Q7/p45S1, producing, respectively, Cyt1Aa (27 kDa) and Cyt1Aa and BinA/BinB (42 kDa/51 kDa) parasporal bodies have been described previously (47, 63). All strains were maintained on Nutrient agar (Becton Dickinson, Sparks, Md.) throughout the study. LB medium (Becton Dickinson, Sparks, Md.) was used for growing *E. coli* and extracting plasmid DNA using the Wizard Plus Mini-prep DNA Purification system (Promega). Genomic DNA was extracted using the DNeasy Blood and Tissue Kit (Qiagen).

Construction of pBU-cyt1Aa-binA. To make a construct that synthesizes the Cyt1Aa-BinA chimera, plasmid pWF53 (64) was digested with SalI and HindIII (FastDigest, Thermo Scientific) and the 1.4-kb fragment that contains the cry1Ac promoter controlling expression of the 20-kDa chaperone-like gene was ligated into plasmid pBU4 (65) digested with the same enzymes and treated with FastAP alkaline phosphatase (Thermo Scientific) to generate plasmid pBU-Pcry1Ac-20 kDa (8.8 kbp). A 0.84-kb fragment containing the cyt1Aa BtIII promoter (66, 67) and the cyt1Aa open reading frame (ORF) was obtained by PCR using the Phire Hot Start II polymerase (Thermo Scientific), primer pair CytF: 5'-gggtaccATTTGATAATAATTGCAAGTTTAAA ATCAT-3' (SEQ ID NO. 3) and Cyt1R 5'-gggcgccaagctt GAGGGTTCCATTAATAGCGCTAGTAAGACTG-3' (SEQ ID NO. 4) and 4Q5 genomic DNA preparation which contained template pBtoxis (68). The amplicon was digested with KpnI and HindIII. Similarly, a 1.4-kbp PCR amplicon containing the binA ORF and Bin transcription terminator (69) was obtained by PCR using Ls 2362 genomic DNA and the primer pair DB42F 5'-aaagcttggcgccATGAGAAA TTTGGATTTTATTGATTC-3' (SEQ ID NO. 5) and DB42R 5'-ggtcgacAAACAACAACAGTTTACATTCGAGTG-3 (SEQ ID NO. 6). The amplicon was digested with HindIII and SalI. To generate pBU-cyt1Aa-binA (FIG. 1A), pBU-20 kDa was digested with KpnI and SalI, treated with FastAP (Thermo Scientific), and ligated to the 0.84 kbp KpnI/HindIII and 1.4 kbp HindIII/SalI digested fragments.

Transformation. Bti 4Q7 was transformed by electroporation as previously described (66), and transformants (4Q7/pBU-cyt1Aa-binA) were selected on LB agar with tetracycline (3 μg/ml) at 28° C.

Culturing bacterial strains and purification of parasporal bodies. Ls 2362 was grown in MBS broth (26), and Bti strains 4Q5, 4Q7/pWF45, 4Q7/pBU-cyt1Aa-binA, and 4Q7/p45S1 were grown in 50 ml of NBG (71) appropriately supplemented with 25 μg/ml erythromycin and 3 μg/ml tetracycline, at 28° C. for 4 days by which time >95% of the cells had sporulated and lysed. Spores and crystals were collected by centrifugation at 6,500 g for 15 min, washed 2× in double-distilled (dd) H$_2$O, followed by centrifugation at 6,500 g for 15 min at 4° C. after each wash, and lyophilized (FreezeZone 4.5, Labconco) for storage.

To isolate parasporal bodies, spore/parasporal body mixtures collected from 50 ml cultures were resuspended in 15 ml ddH$_2$O and sonicated twice at 50% duty cycle for 15 s using the Ultrasonic Homogenizer 4710 (Cole-Parmer Instrument Co.). Five-milliliter samples were loaded onto a sucrose gradient cushion (30-65% w/v), which was then centrifuged at 20,000 g for 45 min at 20° C. in a Beckman L7-55 ultracentrifuge using the SW28 rotor. Bands containing parasporal bodies were collected and washed twice in ddH$_2$O, followed by centrifugation at 6,500 g for 15 min at 4° C. after each wash and lyophilized for storage.

Western blot analysis. Purified parasporal bodies (~10 μg) were solubilized in alkaline buffer (50 mM Na$_2$CO$_3$, pH 11) (70) and protein concentration was determined by the method of Bradford (72), as described previously. Protein samples (0.75 μg and 1.5 μg) were fractionated by electrophoresis in an SDS-10% polyacrylamide gel and electroblotted onto a polyvinylidene difluoride membrane (Micron-Separations, Inc.) using a model PS50 electroblotter (Hoefer Scientific Instruments). Western blot analysis was performed using primary rabbit anti-BinA and anti-Cyt1Aa antibodies and alkaline phosphatase-conjugated goat anti-rabbit immunoglobulin G (Southern Biotechnology Associates, Inc., Birmingham, Ala.) as the secondary antibody as described previously (73). Binding of the secondary antibody was detected with the nitroblue tetrazolium and 5-bromo-1-chloro-3-indolyl phosphate (BCIP) reagents (Promega).

Trypsin digest. Approximately 2 μg of purified parasporal bodies were solubilized in 25 μl 50 mM NaOH, 25° C. for 10 min, followed by addition of 25 μl of 50 mM HCl. Samples were spun at 16,000 g for 5 min, supernatants collected, and trypsin digest of solubilized protoxins was performed as described previously (70).

Microscopy. Sporulating cultures were monitored and photographed with a DMRE phase-contrast microscope (Leica) at a magnification of 1,000×. For preliminary histological studies, control, moribund, and dead larvae (LC$_{95}$ level) were fixed, dehydrated, and embedded in Epon-Araldite (74). Sections 0.25-0.50 μm thick were cut and examined with the above phase contrast microscope.

Bioassays. Lyophilized cultures containing spores and parasporal bodies of the Bti and Ls strains were resuspended in ddH$_2$O. Suspensions were diluted to 6 to 7 different concentrations, ranging from 0.5 ng/ml to 1 μg/ml, in 6 oz cups in a final volume of 100 ml. Bioassays were replicated three times using 30 fourth-instars of S-Lab (Bin-sensitive) and BS-R (Bin-resistant) strains of *Cx. quinquefasciatus*, *Ae. aegypti*, *An. gambiae* (courtesy of B. J. White, Department of Entomology, University of California, Riverside, Calif.) and *An. stephensi* (courtesy of A. A. James, Department of Molecular Biology and Biochemistry, University of California, Irvine) per concentration. After 24 h of exposure at 28° C., dead larvae were counted and the 50% and 95% lethal concentrations, respectively, LC$_{50}$ and LC$_{95}$, were calculated by Probit analysis (POLO-PC; LeOra Software, Berkeley, Calif.) (75).

EXAMPLE 3

Spinosads, a biopesticide consisting of spinosyn A and D, is produced by a naturally occurring, soil-dwelling bacterium, *Saccharopolyspora spinosa* Mertz and Yao. As a new class of polyketide-macrolide insecticides, spinosad has pesticidal activity after ingestion and cuticle absorption against a broad spectrum of susceptible insect species, acting at the nicotinic acetylcholine (nAChR) and γ-aminobutyric acid receptors, causing rapid excitation of the insect nervous system. High resistance to spinosad occurred in response to laboratory selection in *Culex quiquefasciatus*. The resistance ratio after 70 generations of selection reached 52,330-66,447 fold at LC$_{50}$ and 2,934,136-3,522,789 fold at LC$_{90}$ as compared with susceptible reference population. Cross resistance to *Lysinibacillus sphaericus* (VectoLex and Spheratax) evolved simultaneously upon development of resistance to spinosad, which reached 81-125 fold at LC$_{50}$ and 9,471-20,744 fold at LC$_{90}$ during at generations F$_{29-37}$. At generation F$_{55}$, this spinosad-resistant population showed 9.5-34.3 fold cross resistance to *L. sphaericus* 2362 Bin toxins, but only 0.9-1.2 fold cross resistance to a recombinant strain of *B. thuringiensis* (Bt) engineered to produce a chimeric protein consisting of Cyt1Aa fused to BinA, the latter being the toxic moiety of the *L. sphaericus* binary mosquitocidal protein. These results indicate that recombinant bacterial insecticides containing the Bt Cyt1Aa protein can be useful in managing resistance to spinosad compounds.

REFERENCES

The following publications are incorporated by reference herein in their entireties:
1. WHO Factsheet on the World Malaria report, December (2014), on the World Wide Web at who.int/malaria/media/world_malaria_report 2014/en/
2. Huang Y J, Higgs S, Horne K M, Vanlandingham D L (2014) Flavivirus-Mosquito Interactions. *Viruses* 6:4703-4730.
3. Mathai D, Vasanthan A G (2009) State of the Globe: Yellow Fever is Still Around and Active *J Glob Infect Dis* 1:4-6.
4. Enayati A, Hemingway J (2010) Malaria management: past, present, and future. *Annu Rev Entomol* 55:569-591.
5. Federici B A, Park H-W, Bideshi D K (2010) Overview of the basic biology of *Bacillus thuringiensis* with emphasis on genetic engineering of bacterial larvicides for mosquito control. *Open Toxinol J* 3:83-100.
6. Berry C (2012) The bacterium, *Lysinibacillus sphaericus*, as an insect pathogen. *J Invertebr Pathol* 109:1-10.
7. Palma L, Muñoz D, Berry C, Murillo J, Caballero P (2014) *Bacillus thuringiensis* toxins: an overview of their biocidal activity. *Toxins* 6:3296-325.
8. Ben-Dov E (2014) *Bacillus thuringiensis* subsp. *israelensis* and its dipteran-specific toxins. *Toxins* 6:1222-1243.
9. Du J, Knowles B H, Li J, Ellar D J (1999) Biochemical characterization of *Bacillus thuringiensis* cytolytic toxins in association with phospholipid bilayer. *Biochem J* 338:185-193.
10. Promdonkoy B, Ellar D J (2000) Membrane pore architecture of a cytolytic toxin from *Bacillus thuringiensis*. *Biochem J* 350:275-282.
11. Wirth M C (2010) Mosquito resistance to bacterial larvicidal toxins. *Open Toxinol J* 3:101-115.
12. Cantón P E, López-Diaz J A, Gill S S, Bravo A, Soberón S (2014) Membrane binding and oligomer membrane insertion are necessary but insufficient for *Bacillus thuringiensis* Cyt1Aa toxicity. *Peptides* 53:286-291.
13. Butko P (2003) Cytolytic toxin Cyt1A and its mechanism of membrane damage: data and hypothesis. *Appl Environ Microbiol* 69:2415-2422.
14. Nicolas L, Nielsen-Leroux C, Charles J-F, Delecluse A (1993) Respective roles of the 42- and 51-kDa components of the *Bacillus sphaericus* toxin overexpressed in *Bacillus thuringiensis*. *FEMS Microbiol Lett* 106:275-280.
15. Charles J-F, Silva-Filha M H, Nielsen-LeRoux C, Humphreys, M J, Berry, C (1997) Binding of the 51- and 42-kDa individual components from the *Bacillus sphaericus* crystal toxin to mosquito larval midgut membranes from *Culex* and *Anopheles* sp. (Diptera: Culicidae). *FEMS Microbiol Letts* 31: 153-159.
16. Darboux I, Nielsen-LeRoux C, Charles J-F, Pauron D (2001) The receptor of *Bacillus sphaericus* binary toxin in *Culex pipiens* (Diptera: Culicidae) midgut: molecular cloning and expression. *Insect Biochem Mol Biol* 31:981-990.
17. Opota O, Gauthier N C, Doye A, Berry C, Gounon P, Lemichez E, Pauron D (2011) *Bacillus sphaericus* binary toxin elicits host cell autophagy as a response to intoxication. *PLoS One* 6(2):e14682.
18. Tangsongcharoen C, Chomanee N, Promdonkoy B, Boonserm P (2015) *Lysinibacillus sphaericus* binary toxin induces apoptosis in susceptible *Culex quinquefasciatus* larvae. *J Invertebr Pathol* 128:57-63.
19. Charles J-F, Darboux I, Pauron D, Nielsen-Leroux C (2005) Mosquitocidal *Bacillus sphaericus*: toxins, genetics, mode of action, use, and resistance mechanisms. In: Gilbert K L, ed. Elsevier Pergamon. pp 207-231.
20. Yuan Z M, Zhang Y M, Liu E Y (2000) High-level field resistance to *Bacillus sphaericus* C3-41 in *Culex quinquefasciatus* from Southern China. *Biocontrol Sci Technol* 10:43-51.
21. Su T, Mulla M S (2004) Documantation of high-level *Bacillus sphaericus* 2362 resistance in field populations of *Culex quinquefasciatus* breeding in polluted water in Thailand. *J Am Mosq Control Assoc* 20:405-411.
22. Silva-Filha M H, Nielsen-LeRoux C, Charles J-F (1999) Identification of the receptor for *Bacillus sphaericus* crystal toxin in the brush border membrane of the mosquito *Culex pipiens* (Diptera: Culicidae). *Insect Biochem. Mol Biol* 29: 711-721.
23. Romão T P, de Melo Chalegre K D, Key S, Ayres C F, Fontes de Oliveira C M, de-Melo-Neto O P, Silva-Filha M H (2006) A second independent resistance mechanism to *Bacillus sphaericus* binary toxin targets its alpha-glucosidase receptor in *Culex quinquefasciatus*. *FEBS J* 273: 1556-1568.
24. Wirth M C, Georghiou G P, Federici B A (1997) CytA enables CryIV endotoxins of *Bacillus thuringiensis* to overcome high levels of CryIV resistance in the mosquito, *Culex quinquefasciatus*. *Proc Natl Acad Sci USA* 94:10536-10540.
25. Wirth M C, Federici B A, Walton W E (2000) Cyt1A from *Bacillus thuringiensis* synergizes activity of *Bacillus sphaericus* against *Aedes aegypti* (Diptera: Culicidae). *Appl Environ Microbiol* 66:1093-1097.
26. Wirth M C, Walton W E, Federici B A (2000) Cyt1A from *Bacillus thuringiensis* restores toxicity of *Bacillus sphaericus* against resistant *Culex quinquefasciatus* (Diptera: Culicidae). *J Med Entomol* 37:401-407.
27. Wirth M C, Park H-W, Walton W E, Federici B A (2005) Cyt1A of *Bacillus thuringiensis* delays evolution of resistance to Cry11A in the mosquito *Culex quinquefasciatus*. *Appl Environ Microbiol* 71:185-189.
28. Park H-W, Bideshi D K, Wirth M C, Johnson J J, Walton W E, Federici B A (2005) Recombinant larvicidal bacteria with markedly improved efficacy against *Culex* vectors of West Nile virus. *Am J Trop Med Hyg* 72:732-738.
29. Federici B A, Park H-W, Bideshi D K, Wirth M C, Johnson J J, Sakano Y, Tang M (2007) Developing recombinant bacteria for control of mosquito larvae. *J Am Mosq Control Assoc* 23:164-175.
30. Wu D, Chang F N (1985) Synergism in mosquitocidal activity of 26 and 65 kDa proteins from *Bacillus thuringiensis* subsp. *israelensis* crystal. *FEBS Lett* 190:232-236.
31. Ibarra J E, Federici B A (1986) Isolation of a relatively nontoxic 65-kilodalton protein inclusion from the parasporal boady of *Bacillus thuringiensis* subsp. *israelensis*. *J Bacteriol* 165:527-533.

32. Crickmore N, Bone E J, Williams J A, Ellar D J (1995) Contribution of the individual components of the δ-endotoxin crystal to the mosquitocidal activity of *Bacillus thuringiensis* subsp. *israelensis*. *FEMS Microbiol Lett* 131:249-254.
33. Poncet S, Delecluse A, Klier Am Rapoport G (1995) Evaluation of synergistic interactions among the CryIVA, CryIVB, and CryIVD toxic components of *B. thuringiensis* subsp. *israelensis* crystals. *J Invertebr Pathol* 66:131-135.
34. Butko P, Huang F, Pusztai-Carey M, Surewicz W K (1996) Membrane permeabilization induced by cytolytic δ-endotoxin CytA from *Bacillus thuringiensis* var. *israelensis*. *Biochemistry* 35:11355-11360.
35. Butko P, Huang F, Pusztai-Carey M, Surewicz W K (1997) Interaction of the δ-endotoxin CytA from *Bacillus thuringiensis* var. *israelensis* with lipid membranes. *Biochemistry* 36:12862-12868.
36. Manceva S D, Pusztai-Carey M, Russo P S, Butko P (2005) A detergent-like mechanism of action of the cytolytic toxin Cyt1A from *Bacillus thuringiensis* var. *israelensis*. *Biochemistry* 44:589-597.
37. Tharad S, Iturri J, Moreno-Concerrado A, Mittendorfer M, Promdonkoy B, Krittanai C, Toca-Herra J L (2015). Effect of the concentration of cytolytic protein Cyt2Aa2 on the binding mechanism on lipid bilayers studied by OCM-D and AFM. *Langmuir* 31:10477-10483.
38. Cohen S, Albeck S, Ben-Dov E, Cahan R, Firer M, Zaritsky A, Dym O (2011) Cyt1Aa toxin: Crystal structure reveals implications for its membrane-perforating function. *J Mol Biol* 413:804-81.
39. Rodriguez-Almazan C, Ruiz de Escudero I, Canton P E, Munoz-Garay C, Perez C, Gill S S, Soberón M, Bravo A (2010) The amino- and carboxyl-terminal fragments of the *Bacillus thuringensis* Cyt1Aa toxin have differential roles in toxin oligomerization and pore formation. *Biochemistry* 50:388-396.
40. Knowles B H, Ellar D J (1987) Colloid-osmotic lysis is a general feature of the mechanism of action of *Bacillus thuringiensis* δ-endotoxins with different insect specificities. *Biochim Biophys Acta* 924:509-518.
41. Knowles B H, Blatt M R, Tester M, Horsnell J M, Carroll J, Menestrina G, Ellar D J (1989) Acytolytic δ-endotoxin from *Bacillus thuringiensis* var. *israelensis* forms cation-selective channels in planar lipid bilayers. *FEBS Lett* 244:259-262.
42. Knowles B H (1994) Mechanism of action of *Bacillus thuringiensis* insecticidal δ-endotoxins. *Adv Insect Physiol* 24:275-30.
43. Al-yahyaeet S A, Ellar D J (1995) Maximal toxicity of cloned CytA & endotoxin from *Bacillus thuringiensis* subsp. *israelensis* requires proteolytic processing from both the N- and C-termini. *Microbiology* 141:3141-3148.
44. Clark M A, Baumann P (1990) Deletion analysis of the 51-kilodalton protein of the *Bacillus sphaericus* 2362 binary mosquitocidal toxin: Construction of derivatives equivalent to the larva-processed toxin. *J Bacteriol* 172: 6759-6763.
45. Nicolas L, Lecroisey A, Charles J F (1990) Role of the gut proteinases from mosquito larvae in the mechanism of action and the specificity of the *Bacillus sphaericus* toxin. *Can J Microbiol* 36:804-807.
46. Darboux I, Pauchet Y, Castella c, Silva-Filha M H, Nielsen-LeRoux, Charles J-F, Pauron D. (2002) Loss of a membrane anchor as of the target receptor is a mechanism of bioinsecticides resistance. *Proc Natl Acad Sci USA* 99:5830-5835.
47. Park H-W, Bideshi D K, Federici B A (2003) Recombinant strain of *Bacillus thuringiensis* producing Cyt1A, Cry11B, and the *Bacillus sphaericus* binary toxin. *Appl Environ Microbiol* 69:1331-1334.
48. Pérez C, Fernandez L E, Sun J, Folch J, Gill S S, Soberón M, Bravo A (2005) *Bacillus thuringiensis* subsp. *israelensis* Cyt1Aa synergizes Cry11Aa toxin by functioning as a membrane-bound receptor. *Proc Natl Acad Sci USA* 102:18303-18308.
49. Federici B A, Park H-W, Bideshi D K, Wirth M C, Johnson J J (2003) Recombinant bacteria for mosquito control. *J Exp Biol* 206: 3877-3885.
50. Hire R S, Hadapad A B, Dongre T K, Kumar V (2009) Purification and characterization of mosquitocidal *Bacillus sphaericus* protein. *J Invertebr. Pathol* 101:106-111.
51. Deist B R, Rausch M A, Fernandez-Luna M T, Adang, M J, and Bonning B C (2014) Bt toxin modification for enhanced efficacy. *Toxins* 6:3005-3027.
52. Davidson E W. (1979) Ultrastructure of midgut events in the pathogenesis of *Bacillus sphaericus* strain SSII-1 infections of *Culex pipiens quinquefasciatus* larvae. *Can J Microbiol* 25:178-184.
53. Oei C, Hindley J, Berry C (1992) Binding of purified *Bacillus sphaericus* binary toxin and its deletion derivatives to *Culex quinquefasciatus* gut: elucidation of functional binding domains. *J Gen Microbiol* 138:1515-1526.
54. Boonserm P, Moonsom S, Boonchoy C, Promdonkoy B, Parthasarathy K, Torres J (2006) Association of the components of the binary toxin from *Bacillus sphaericus* in solution and with model lipid bilayers. *Biochem Biophys Res Comm* 342:1273-1278.
55. Limpanawat S, Promdonkoy B, Boonserm P (2009) The C-terminal domain of BinA is responsible for *Bacillus sphaericus* binary toxin BinA-BinB interaction. *Curr Microbiol* 59:509-513.
56. Srisucharitpanit K, Inchana P, Rungrod A, Promdonkoy B (2012) Expression and purification of the active soluble form of *Bacillus sphaericus* binary toxin for structural analysis. *Prot Express Purific* 82:368-372.
57. Kale A, Hire R S, Hadapad A B, D'Souza S F, Kumar V (2013) Interaction between mosquito-larvicidal *Lysinibacillus sphaericus* binary toxin components: Analysis of complex formation. *Insect Biochem Mol Biol* 43:1045-1054.
58. Hire R M, Sharma M, Hadapad A B, Kumar V (2014) An oligomeric complex of BinA/BinB is not formed in-situ in mosquito-larvicidal *Lysinibacillus sphaericus* ISPC-8. *J Invertebr Pathol* 122:44-47.
59. Srisucharitpanit K, Yao M, Promdonkoy B, Chimnarook S, Tanaka I, Boonserm P. (2014) Crystal structure of BinB: A receptor binding component of the binary toxin from *Lysinibacillus sphaericus*. *Proteins* 82:2703-2712.
60. Lekakarn H, Promdonkoy B, Boonserm, P. 2015. Interaction of *Lysinibacillus sphaericus* binary toxin with mosquito larval gut cells: Binding and internalization. *J Invertebr Pathol* 132:125-131.
61. Smith A W. Camara-Artigas A, Brune D C, Allen J P (2005) Implications of high-molecular weight oligomers of the binary toxin from *Bacillus sphaericus*. *J Invertebr Pathol* 88:7-33.
62. Hire R S, Hua G, Zhang Q, Mishra R, Adang A J (2015) *Anopheles gambiae* Ag55 cell line as a model for *Lysinibacillus sphaericus* Bin toxin action. *J Invertebr Pathol* 132:105-110.

63. Wu D, Federici B A (1993) A 20-kilodalton protein preserves cell viability and promotes CytA crystal formation during sporulation in *Bacillus thuringiensis*. *J Bacteriol* 175:5276-80.
64. Wu D, Federici B A (1995) Improved production of the insecticidal CryIVD protein in *Bacillus thuringiensis* using cry1A(c) promoters to express the gene for an associated 20-kDa protein. *Appl Micriobiol Biotech* 42:697:702.
65. Bourgouin C, Delecluse A, de la Torre F, Szulmajster J (1990) Transfer of the toxin protein genes of *Bacillus sphaericus* into *Bacillus thuringiensis* subsp. *israelensis* and their expression. *Appl Environ Microbiol* 56:340-344.
66. Park H-W, Hice R H, Federici B A (2016) Effect of promoters and plasmid copy numbers on Cyt1A synthesis and crystal assembly in *Bacillus thuringiensis*. *Curr Microbiol* 72:33-40.
67. Sakano Y., Park H-W, Ge B, Bideshi D K, Federici B A (2016) Contributions of 5'-UTR and 3'-UTR cis elements to Cyt1Aa synthesis in *Bacillus thuringeinsis* subsp. *israelensis*. Submitted.
68. Berry C, O'Neil S, Ben-Dov E, Jones A F, Murphy L, Quail M A, Holden M T, Harris D, Zaritsky A, Parkhill J (2002) Complete sequence and organization of pBtoxis, the toxin-coding plasmid of *Bacillus thuringiensis* subsp. *israelensis*. *Appl Environ Microbiol* 68:5082-5095.
69. Baumann L, Broadwell A H, Baumann P (1988) Sequence analysis of the mosquitocidal genes encoding 51.4- and 41.9-kilodalton proteins from *Bacillus sphaericus* 2362 and 2297. *J Bacteriol* 170:2045-2050.
70. Bideshi D K, Waldrop G, Fernandez-Luna M T, Diaz-Mendoza M, Wirth M C, Johnson J J, Park H-W, Federici B A (2013) Intermolecular interaction between Cry2Aa and Cyt1Aa and its effect on larvicidal activity against *Culex quinquefasciatus*. *J Microbiol Biotechnol* 23:1107-1115.
71. Park H-W, Bideshi D K, Johnson J J, Federici B A (1999) Differential enhancement of Cry2A versus Cry11A yields in *Bacillus thuringiensis* by use of the cry3A STAB mRNA sequence. *FEMS Microbiol Lett* 181:319-327.
72. Bradford M M (1976) A rapid and sensitive method for the quantitation of microgram quantities of protein utilizing the principle of protein-dye binding. *Anal Biochem* 72:248-254.
73. Park H-W, Federici B A (2000) Domain I plays an important role in the crystallization of Cry3A in *Bacillus thuringiensis*. *Mol Biotechnol* 16:97-107.
74. Lacey, L A, B. A. Federici, B A (1979) Pathogenesis and midgut histopathology of *Bacillus thuringiensis* in *Simulium vittatum* (Diptera: Simuliidae). *J Invertebr Pathol* 33:171-182.
75. Raymond M, Prato G, Ratsira D (1993) Probability analysis of mortality assays showing quantile response, version 3.3. Praxeme, Saint Georges D'argues, France.

Although the present invention has been described in connection with some preferred embodiments, it is to be understood that modifications and variations may be utilized without departing from the principles and scope of the invention, as those skilled in the art will readily understand. Accordingly, such modifications may be practiced within the scope of the invention and the following claims.

---

What is claimed is:

1. A chimeric protein comprising a cytolytic δ-endotoxin portion and a heterologous polypeptide portion, wherein the cytolytic δ-endotoxin portion is Cyt1Aa and the heterologous polypeptide portion is BinA.

2. The chimeric protein of claim 1, wherein the C-terminal end or N-terminal end of the cytolytic δ-endotoxin portion is fused to the heterologous polypeptide portion.

* * * * *